(12) United States Patent
Koga et al.

(10) Patent No.: US 8,198,086 B2
(45) Date of Patent: Jun. 12, 2012

(54) METHOD FOR PRODUCTION OF THREE-DIMENSIONAL STRUCTURE OF CELLS

(75) Inventors: Toshinobu Koga, Fukuoka (JP); Soichi Nagasato, Fukuoka (JP); Yukihide Iwamoto, Fukuoka (JP); Koichi Nakayama, Fukuoka (JP)

(73) Assignee: Kyushu University, National University Corporation, Fukuoka (JP)

( * ) Notice: Subject to any disclaimer, the term of this patent is extended or adjusted under 35 U.S.C. 154(b) by 257 days.

(21) Appl. No.: 12/450,542

(22) PCT Filed: Mar. 31, 2008

(86) PCT No.: PCT/JP2008/056826
§ 371 (c)(1),
(2), (4) Date: Nov. 4, 2009

(87) PCT Pub. No.: WO2008/123614
PCT Pub. Date: Oct. 16, 2008

(65) Prior Publication Data
US 2011/0200559 A1    Aug. 18, 2011

(30) Foreign Application Priority Data
Mar. 30, 2007    (JP) .................. 2007-094313

(51) Int. Cl.
*C12N 5/00* (2006.01)
*C12N 5/02* (2006.01)
*A61F 13/00* (2006.01)
*A61F 2/00* (2006.01)

(52) U.S. Cl. ........ 435/395; 435/396; 435/398; 435/402; 435/373; 424/422; 424/423

(58) Field of Classification Search .................. None
See application file for complete search history.

(56) References Cited

U.S. PATENT DOCUMENTS

| 5,650,164 A | 7/1997 | Della Valle et al. |
| 5,855,619 A | 1/1999 | Caplan et al. |
| 7,704,741 B2 * | 4/2010 | Fuhr et al. ................. 435/400 |

(Continued)

FOREIGN PATENT DOCUMENTS

EP    0470681 A2    2/1992

(Continued)

OTHER PUBLICATIONS

Chua, KN et al., Stable immobilization of rat hepatocyte spheroids on galactosylated nanofiber scaffold. Biomaterials. May 2005, vol. 26 (15), pp. 2537-2547.

(Continued)

*Primary Examiner* — Jon P Weber
*Assistant Examiner* — Charles Zoltan Constantine
(74) *Attorney, Agent, or Firm* — McDermott Will & Emery LLP

(57) ABSTRACT

The present invention provides a method for arranging various cells as cell clusters in an arbitrary three-dimensional space and producing a three dimensional structure of a desired shape constituted exclusively by cells. Furthermore, the present invention provides a support provided with a substrate and a thread or needle-shaped material that penetrates the substrate and cell clusters for positioning cell clusters in arbitrary space. The support is provided with a sheet that can be removed as necessary for covering the substrate. Further, a method for using the support structure to position cell clusters in an arbitrary space and a method for the production of three-dimensional cell structures are provided.

18 Claims, 27 Drawing Sheets
(11 of 27 Drawing Sheet(s) Filed in Color)

U.S. PATENT DOCUMENTS 7,763,272 B2 * 7/2010 Offermann et al. ........... 424/426
2008/0193421 A1 8/2008 Kruse et al.

FOREIGN PATENT DOCUMENTS

| JP | 447422 | 4/1992 |
| JP | 10-505250 | 5/1998 |
| JP | 2004-357694 A | 12/2004 |
| JP | 2006-124346 A | 5/2006 |
| JP | 2007-300870 A | 11/2007 |
| WO | WO-2005/113747 A2 | 12/2005 |

OTHER PUBLICATIONS

International Search Report mailed Jul. 8, 2008 in PCT/JP2008/056826.

Choi et al., "Cell ineraction with three-dimensional sharp-tip nanotopography", Biomaterials, vol. 28, No. 9, pp. 1672-1679 (2006).

Raghunath et al., "Biomaterials and scaffold design: Key to tissue-engineering cartilage", Biotechnology and Applied Biochemistry, vol. 46, No. 2, pp. 73-84 (2007).

Bhatis et al., "Controlling cell interactions by micropattering in co-cultures: Hepatocytes and 3T3 fibroblasts", Journal of Biomedical Materials Research, vol. 34, No. 2, pp. 189-199 (1997).

English translation of Japanese Laid-Open Utility Model Publication No. H04-47422 (Japanese Laid-Open Utility Mode Publication No. H04-47422 was cited in the IDS submitted Feb. 23, 2010).

* cited by examiner

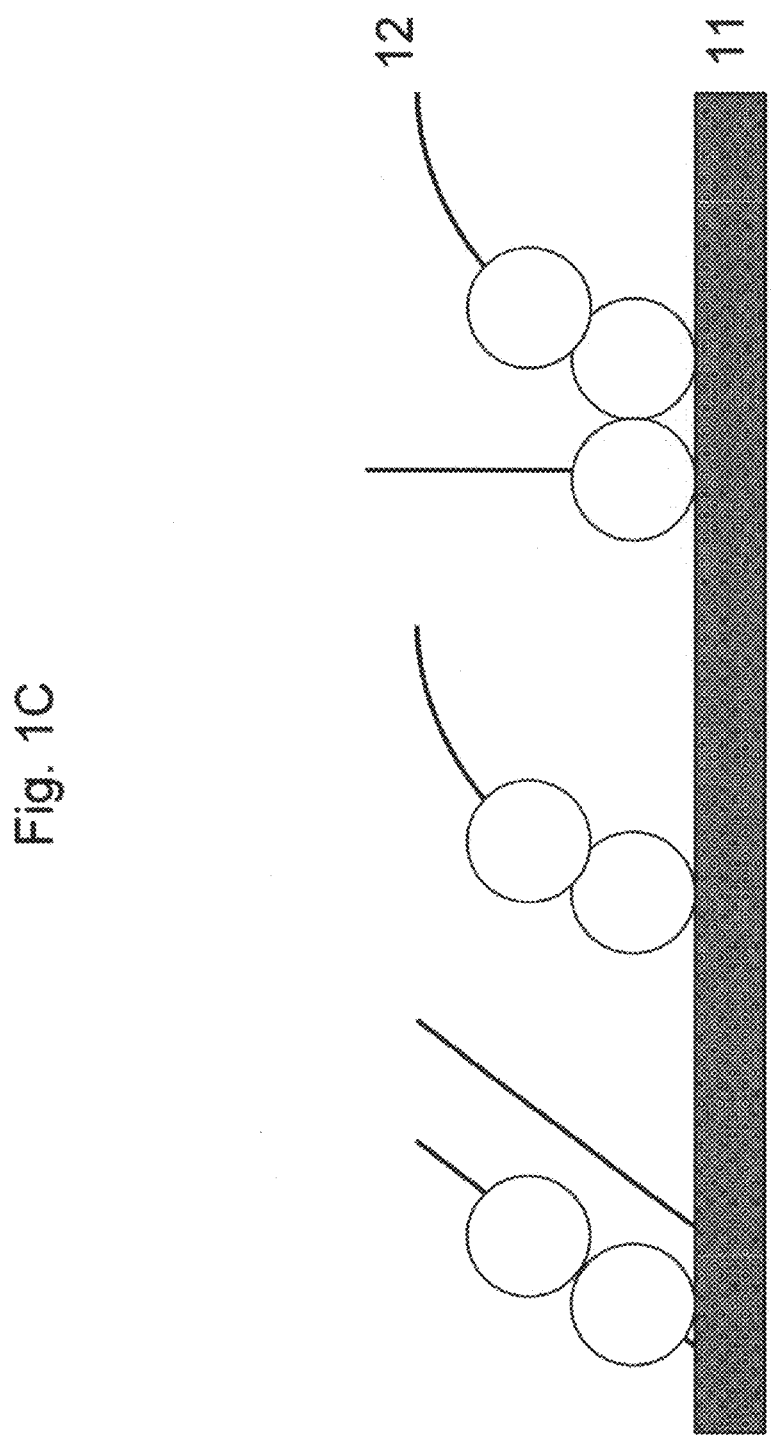

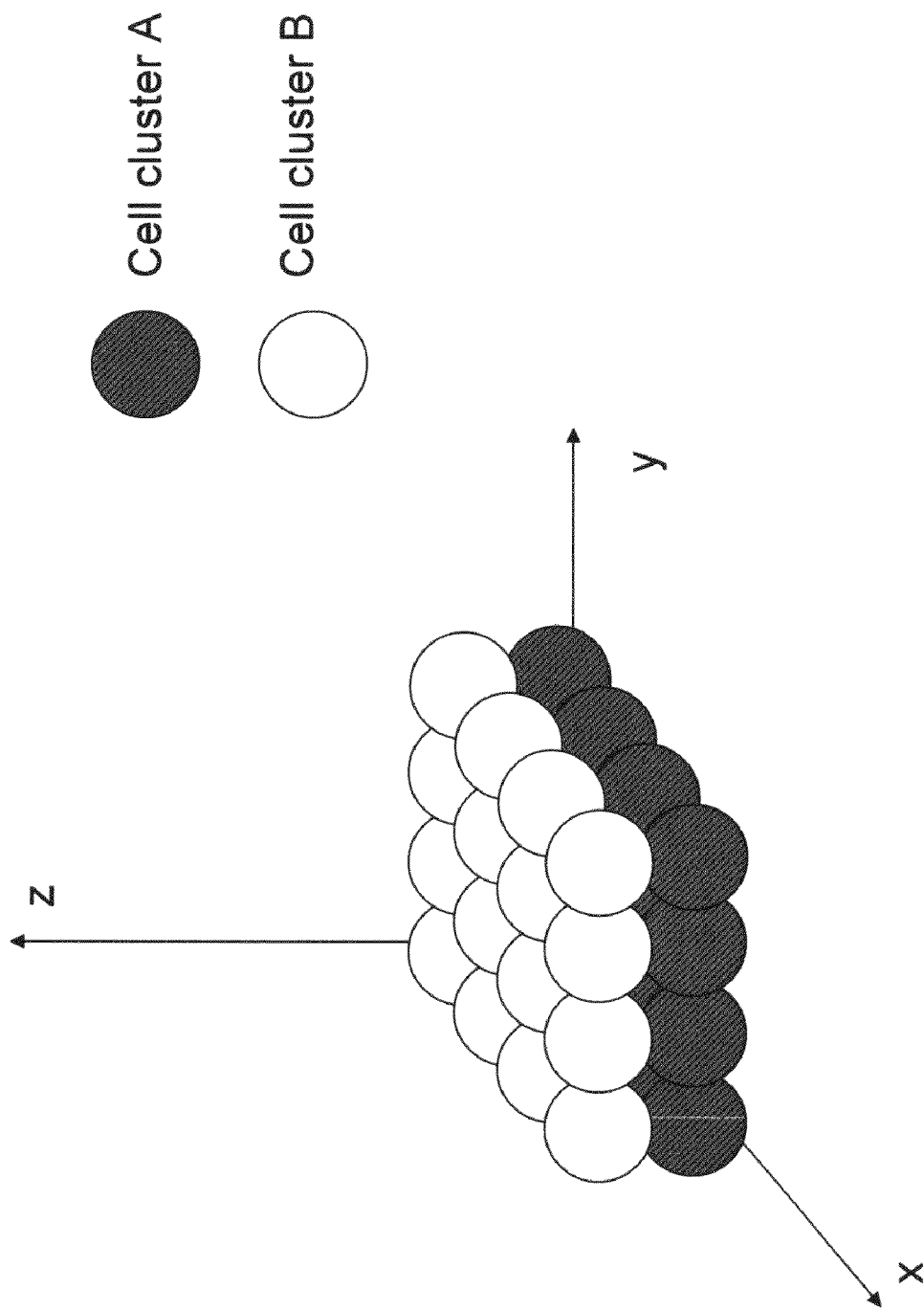

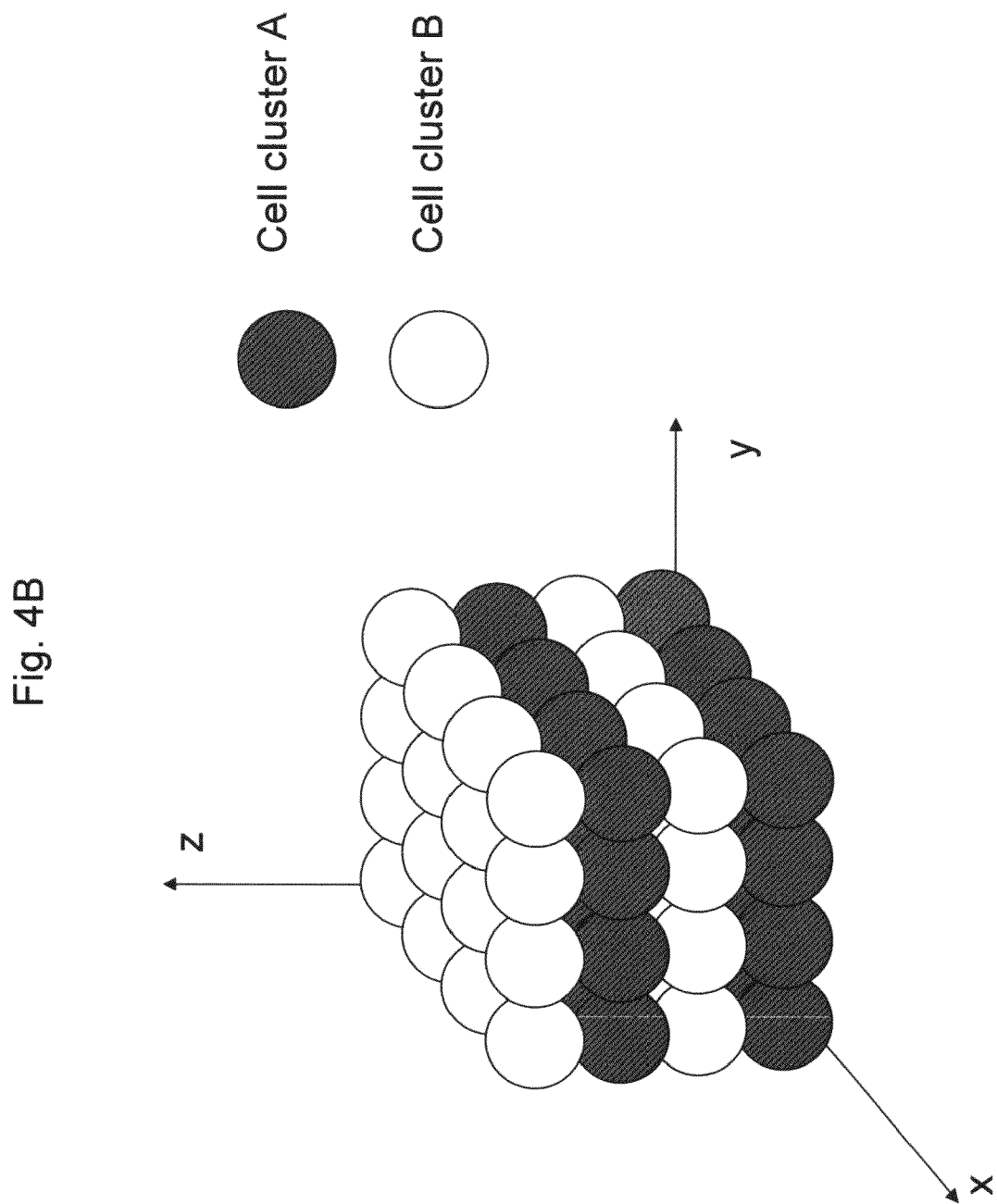

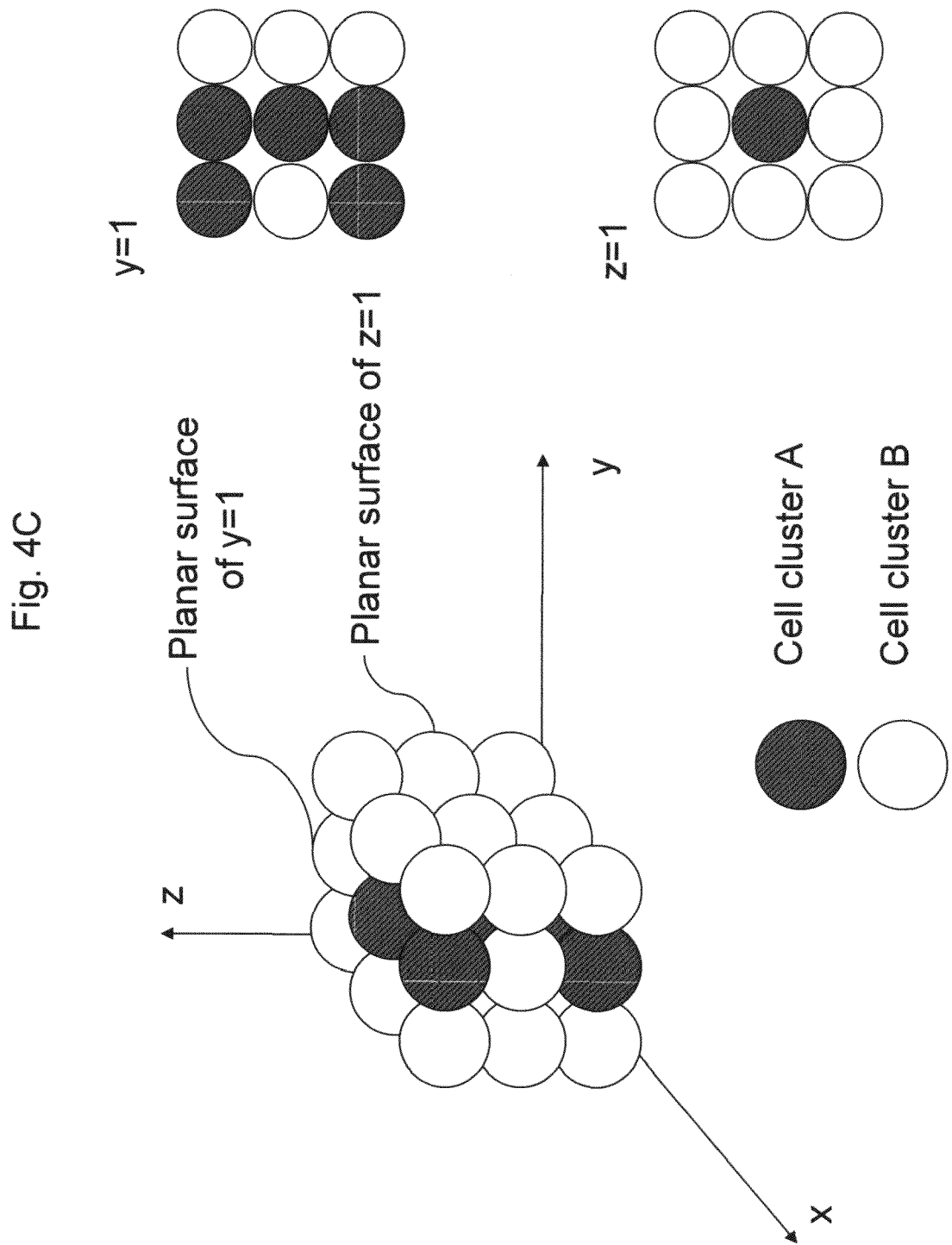

a b a b

METHOD FOR PRODUCTION OF THREE-DIMENSIONAL STRUCTURE OF CELLS

This application is the U.S. national phase application under 35 U.S.C. §371 of International Patent Application No. PCT/JP2008/056826 filed Mar. 31, 2008, which claims the benefit of priority to Japanese Patent Application No. 2007-094313 filed Mar. 30, 2007, the disclosures of all of which are hereby incorporated by reference in their entireties. The International Application was published in Japanese on Oct. 16, 2008 as WO 2008/123614.

FIELD OF THE INVENTION

The present invention relates to a method for positioning various cells in an arbitrary three-dimensional space to create three-dimensional structures composed only of cells and the cell structures created therethrough.

BACKGROUND

Regenerative medicine in which cells are transplanted to an affected area pursuant to the objective of regenerating a lost organ is increasingly in practical use. Conventionally, an absorbent material that would provide the cells with a scaffolding inside the body was necessary to affect regeneration of large organs. Although use of animal-derived collagen and hydrolyzed artificial polymers as these absorbent materials has been tried, adequate effects have yet to be attained in terms of safety and cost. Therefore, the present inventors developed a method in which three-dimensional structures are built entirely from cells (Japanese Laid-Open Publication 2004-357694, "Tissue Plug Production Method"). In this method, by pouring a cell cluster into a mold, the creation of large structures composed only of cells, which was conventionally held to be extremely difficult, was achieved. This invention has had its efficacy confirmed in animal experiments, has progressed to the initial phase of clinical application, and is attracting attention.

According to the above-mentioned cell plug production method, by pouring cell clusters of different strains into a culture vessel, etc. in order, it is possible to create a layer-like complex cell structure. However, since organs have an even more complex sequence structure of cells, the development of a method for creating cell plugs that can assume a more arbitrary sequence structure is necessary. Further, as cell structures grow larger and more complex, supply of culture medium to the structure interior (during culturing) and blood vessel channels must be secured and further improved when performing large organ regeneration thereafter.

In recent years, special gelatin that hardens at approximately 37 degrees and turns to liquid at low temperatures has been developed (temperature-sensitive gelatin). Attempts are being made to construct three-dimensional cell structures by adhering cells to this gelatin to create cell sheets, and further stacking cell sheets upon one another. However, supplying culture medium to the interior of the cell structures is extremely difficult through the use of this method, and the thickness of structure appears to be limited to approximately 2 mm. Further, according to this method, following completion of the structure, gelatin can be recovered from the interior of the structure after the temperature has been lowered to convert the temperature-sensitive gelatin into a liquid. However, it is doubtful that gelatin can be completely recovered from inside the structures, and residual gelatin in the body presents a risk of side effects due to foreign-body reaction (Regeneration of Cartilage Tissues Using Mebiol® Gel Internet at www.mebiol.co.jp/rd-img/nankotu.pdf).

DETAILED DESCRIPTION

The purpose of the present invention is to provide a method for positioning various cells in an arbitrary three-dimensional space and producing three dimensional structures constituted exclusively by cells.

As a result of diligent research undertaken to solve the above-mentioned problem, the present inventors have, through the use of the temporary immobilization support structure of the present invention, positioned various cells in an arbitrary three-dimensional space, succeeded in the creation of three-dimensional structures composed only of cells, and completed the present invention.

In other words, the present invention is as described below.
(1) A support for positioning cell clusters in arbitrary space, wherein said support is provided with a substrate and thread or needle-shaped materials (puncturing structures) for puncturing cell clusters.
(2) The support described in (1) wherein the thread or needle-shaped materials are positioned on the substrate in an almost perpendicular direction.
(3) The support described in (1) or (2) further provided with a sheet covering the substrate.
(4) The support described in claim 1 or 2 wherein the thread or needle-shaped materials are non-cell-adherent.
(5) The support described in (1) or (2) wherein the thread or needle-shaped materials are spaced apart on the support such that they can contact the neighboring cell clusters when cell clusters are punctured.
(6) The support described in (3) wherein the sheet is non-cell-adherent.
(7) The support described in (3) wherein the sheet is provided with holes or is mesh so that it can be penetrated by the thread or needle-shaped structures immobilized to the substrate.
(8) The support described in (1) or (2) wherein the cell clusters are spheroids.
(9) The support according to (1) or (2) wherein the needle-shaped material is conical.
(10) The support described in (1) or (2) wherein the thread or needle-shaped materials are made of polypropylene, nylon, or stainless steel.
(11) The support described in (3) wherein the sheet is treated with either fluorine or polyhydroxyethylmethacrylate.
(12) A method for positioning cell clusters in arbitrary spaces, said method comprising:
    a) the step of forming cell clusters;
    b) the step of penetrating the formed cell clusters with the thread or needle-shaped materials of the support described in claim 1; and
    c) the step of causing the penetrated cell clusters to contact each other.
(13) A method for the production of cell structures, said method comprising:
    a) the step of forming cell clusters;
    b) the step of penetrating the formed cell clusters with the thread or needle-shaped materials of the support described in claim 1;
    c) the step of causing the penetrated cell clusters to contact each other; and
    d) the step of recovering the cell clusters that contacted each other.

(14) The method described in (12) or (13) wherein the cell clusters are penetrated by the thread or needle-shaped materials so that they continuously make contact with each other in the longitudinal direction.

(15) The method described in (13) wherein the recovery of contacted cell clusters is attained by the step of drawing the support from fused cell clusters.

(16) The method described in any one of (12) to (15) wherein the cell cluster is a spheroid.

(17) A cell structure produced according to the method described in any one of (12) to (15).

(18) The cell structure described in (17) wherein the cell structure is constituted by same types of cells.

(19) The cell structure described in (17) wherein the cell structure is constituted by multiple types of cells.

(20) The cell structure described in any one of (17) to (19) that is used medically or experimentally.

(21) The cell structure described in (20) used in the regeneration of joints.

SUMMARY OF THE INVENTION

The present invention provides a support for positioning cell clusters in arbitrary space and a method for the production of cell structures consisting only of cells without remaining foreign substances by removing the support after the structure is formed, wherein the above-mentioned support is used to place each type of cell in an arbitrary three-dimensional space, and the structure is formed through the fusion/bonding of cells with one another. It is known that cell clusters (spheroids) fuse together when left alone when in close proximity to one another. Through the use of the support and methods of the present invention, the shape of the structures formed by spheroid fusion can be controlled, and cell clusters can be placed in the desired position in an arbitrary three-dimensional space. Further, according to the present invention, a void (tunnel) can be provided within the cell structure (at the interior walls of the structure formed from cell clusters) by not placing cell clusters where the void is desired, and culture solution can be supplied to said tunnel. As a result, large cell structures can be formed. The obtained cell structures can be used, for example, in medical cell transplantation pursuant to the objective of organ regeneration. Further, use in organ simulations for research such as in vitro drug screening is also possible.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1C shows the support 10 of the present invention having various types of thread or needle-shaped material 12.

FIG. 4A is a drawing showing an example of a cell structure constituted by two types of cell cluster. In this illustrated embodiment, a chimera cell structure comprising cell cluster A and cell cluster B is provided at the support, where the cell clusters are arranged in a grid pattern, a first row of needle-shaped materials penetrates cluster A, a second row of needle-shaped materials penetrates cluster B, and the preceding are fused.

FIG. 4B is a drawing showing another example of a cell structure composed of two types of cell cluster. In this illustrated embodiment, a structure in which cell cluster A and cell cluster B form alternating layers can be produced by alternately applying both cell clusters so that cell cluster A is added to a third row of needle-shaped materials, and cell cluster B is added to a fourth row of needle-shaped materials in addition to the above-described first row and second row (FIG. 4A).

FIG. 4C is a drawing showing a different example of a cell structure composed of two types of cell cluster. In this illustrated embodiment, a structure in which cell cluster A and cell cluster B form alternating layers can be produced by alternately applying both cell clusters so that cell cluster A is added to a third row of needle-shaped materials, and cell cluster B is added to a fourth row of needle-shaped materials in addition to the above-described first row and second row (FIG. 4B). It is also possible to change the type of cell cluster that is being penetrated by a single needle-shaped material.

DESCRIPTION OF SYMBOLS

10: Support
11: Substrate
12: Thread-shaped or needle-shaped material
13: Sheet

Embodiments of the present invention are explained hereinbelow. Embodiments described below are provided only for illustrative purposes and the present invention is not intended to be limited thereto. The present invention can be practiced in various forms without departing from the spirit of the present invention.

All publications, for example prior art documents, laid-open publications, patents and other patent documents cited in this specification are incorporated herein by reference in their entirety. This patent specification includes the entirety of the specification of Japanese patent application No. 2007-094313 (date of filing: Mar. 30, 2007), which forms the basis for the priority claim of this application.

The present invention is explained in detail hereinbelow.

1. Support

Figure 1A:
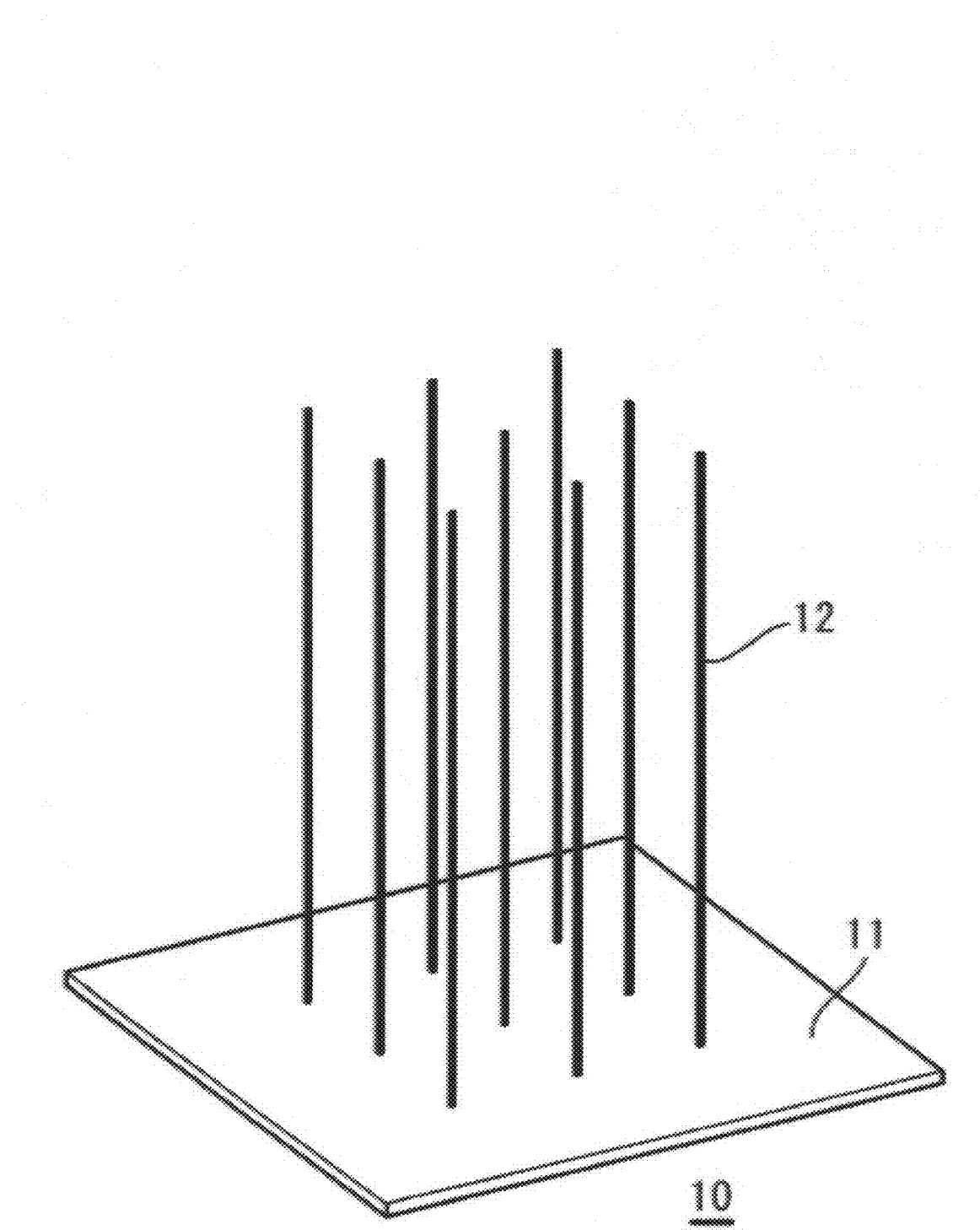
FIG. 1A shows the main body of support 10 of the present invention, in an embodiment wherein the thread or needle-shaped material 12 is positioned in almost the perpendicular direction of the basal surface of the substrate 11.
Figure 1B:
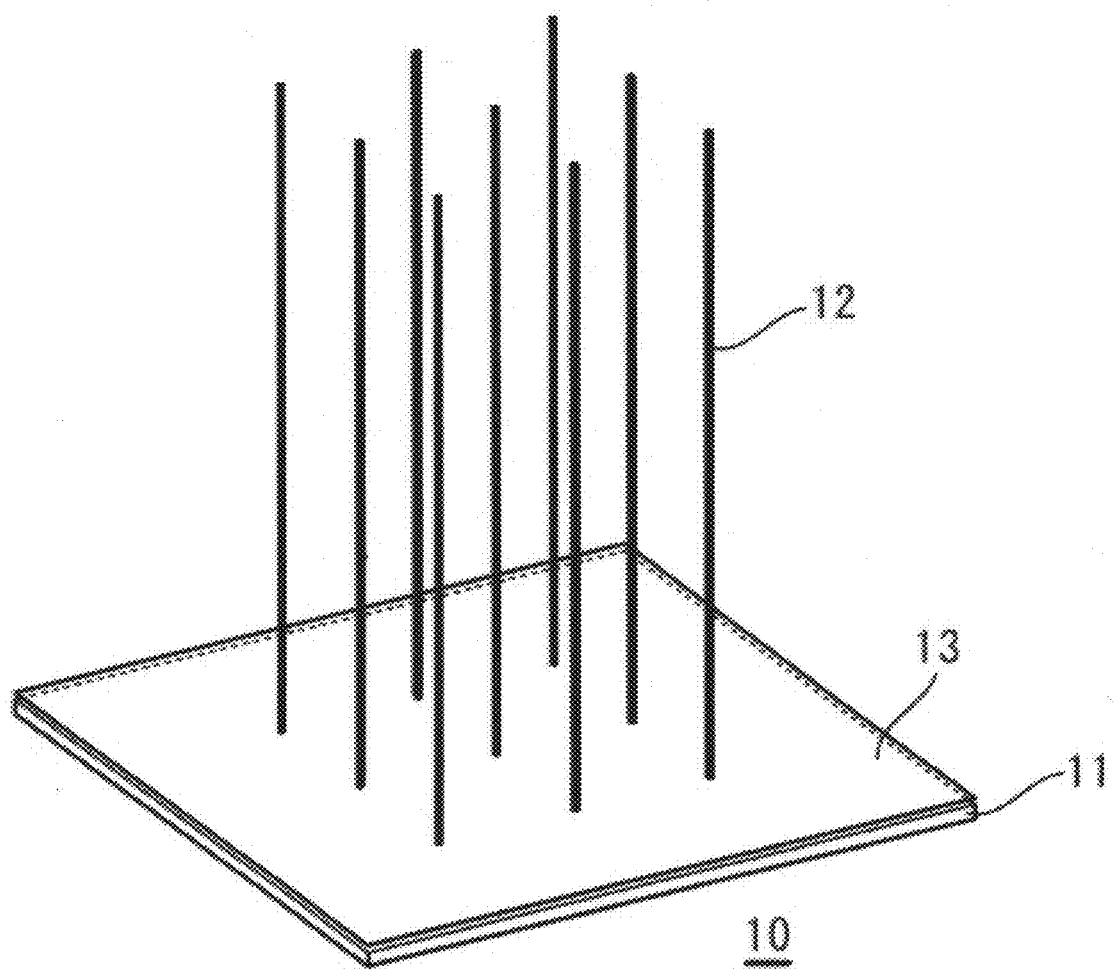
FIG. 1B shows the support 10 of the present invention provided with a sheet atop the basal surface of a substrate. Substrate 11 is provided with a sheet 13 that covers the surface of the substrate on which thread-shaped or needle-shaped materials 12 exist.

One embodiment of the support of the present invention is shown in FIG. 1A and FIG. 1B. In FIG. 1A, the main body of support 10 is provided with substrate 11 and thread or needle-shaped material 12. The main body of support 10 is provided with substrate 11 having an arbitrary shape, and thread or needle-shaped material 12 atop substrate 11. FIG. 1A is an illustrative embodiment of an example wherein the thread or needle-shaped material is positioned in almost the perpendicular direction of the basal surface of the substrate. The entirety of substrate 11 and thread-shaped or needle-shaped material 12 may be composed of separate parts and fixed or made from a single piece of material such as thermoplastic resin. Further, the quantity of thread-shaped or needle-shaped materials on the support is one or more, and a desired number of thread-shaped or needle-shaped materials of arbitrary quantity may be used. As used herein, the phrase "in an almost perpendicular direction" means that the longitudinal angle of the thread-shaped material or needle-shaped material is at an arbitrary angle of approximately 90° in relation to the basal surface of substrate 11, preferably 90°. In another embodiment, substrate 11 is further provided with a sheet 13 that covers the surface of the side of substrate 11 on which thread-shaped or needle-shaped materials exist (FIG. 1B). The surface area of sheet 13 may be smaller than, identical to, or larger than the surface area of the basal surface of substrate 11, but will preferably cover the region at which thread or needle-shaped materials exist.

In still another embodiment of the present invention, thread or needle-shaped materials can be positioned in the non-perpendicular direction (e.g., a direction having an angle from the perpendicular direction) as opposed to the perpendicular direction. The angle of the thread or needle-shaped materials in the "non-perpendicular direction" can be selected as appropriate from the range of 1° to 89°, for example, 10°, 20°, 30°, 40°, 50°, 60°, 70°, and 80° in relation to the body of support 10. Further, the thread or needle-shaped materials in "the non-perpendicular direction" may extend from the support straight in a given direction or extend in a curve such as a part of the arc of a circle or an ellipse (FIG. 1C). It is not necessary for the thread or needle-shaped materials that exist on the support to have a uniform shape; various shapes of thread or needle-shaped materials can be used in combination (FIG. 1C). These aspects include but are not limited to supports that are a combination of thread or needle-shaped materials in the perpendicular direction and thread or needle-shaped materials having a fixed angle in the non-perpendicular direction; supports that are a combination of thread or needle-shaped materials in the perpendicular direction and thread or needle-shaped materials having a locus corresponding to a portion of an arc; and supports that are a combination of thread or needle-shaped materials in the perpendicular direction or thread or needle-shaped materials having a fixed angle in the non-perpendicular direction; and thread or needle-shaped materials having a locus that corresponds to a portion of an arc. For example, if a thread or needle-shaped material is a curved line, is arranged atop a circle to form an arch, and cell clusters are penetrated and fused along the arch, a bowl-shaped cell structure, can, for example, be constructed. Further, if a thread or needle-shaped material is a straight line, a conical shape, hollow shape, or pyramid shape can be formed, depending on the arrangement of the thread or needle-shaped materials. Cell structures with complex shapes can be formed by using a combination of multiple thread or needle-shaped material shapes.

It is preferable that thread or needle-shaped material 12 and sheet 13 all be made of non-cell-adherent material. Although it is preferable that the substrate also be non-cell-adherent, when a sheet 13 is used, cell clusters do not make direct contact with substrate 11, so the material thereof is not relevant. The term "non-cell-adherent" means a property that prevents cells from adhering to wall surfaces through the extracellular adhesion factor. Substances coated with material that imparts cell non-adhesive properties (i.e. fluorine) have the above-mentioned property. In a preferable embodiment, thread or needle-shaped material 12 is made of either polypropylene, nylon, or stainless steel. In another preferable embodiment, sheet 13 is treated with either fluorine or polyhydroxyethylmethacrylate polymer (poly-HEMA treated). For the thread or needle-shaped material 12 and sheet 13 of the present invention, engineering plastics such as TEFLON®, poly-HEMA, an acrylic plate, a vinyl chloride plate, an ABS resin plate, a polyester-based resin plate, polycarbonate plate, PP (polypropylene), ABS (acrylonitrile butadiene styrene), PE (polyethylene), POM (polyacetal), PC (polycarbonate), PEEK (polyether ether ketone), MCN (monomer casting nylon) 6N (6 nylon), 66N (66 nylon) are also acceptable. Other materials that lower cell adherence can be used; materials are not limited to these. Although use of bioabsorbable material for the above-mentioned support can also be considered, if bioabsorbable material is used, degradation products and residue that did not completely dissolve may remain and exhibit toxicity. Therefore, the above-mentioned materials are preferable to bioabsorbable material.

The thread or needle-shaped material 12 are rod-shaped materials for puncturing cell clusters so they are in a so-called skewered form. The position of each thread or needle-shaped material is determined so that the space between cell clusters is such that each cell cluster penetrated by a thread or needle-shaped material can make mutual contact with and fuse with the cell clusters neighboring it. Thread or needle-shaped materials may be arranged in, for example, an orderly grid or at random. Although the space between individual thread or needle-shaped materials may vary according to the size of the cell clusters they penetrate, the length of said space is preferably stipulated as approximately 100% to 110% of the cell cluster diameter. For example, if the diameter of a cell cluster is 1 mm, an approximate 1 mm to 1.1 mm space between individual thread or needle shaped materials is preferable.

Figure 1D:
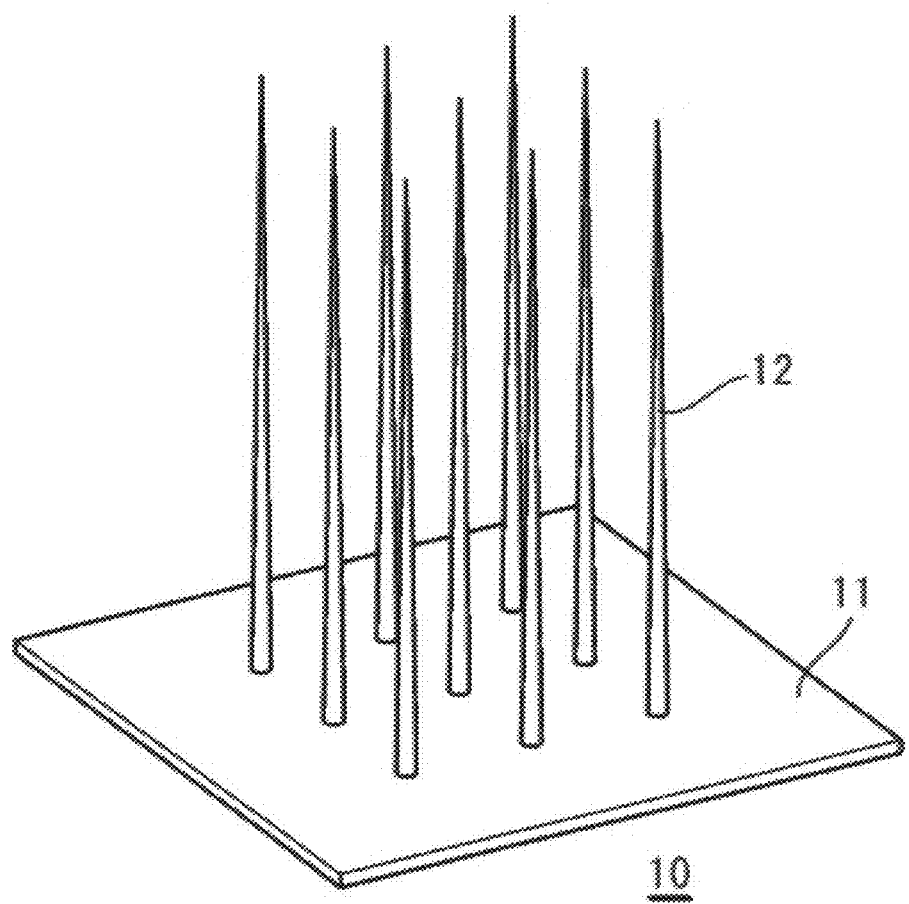
FIG. 1D shows a drawing of an embodiment wherein the needle-shaped materials 12 extending from the substrate 11 are conical.

The diameter of a cross-section of a thread or needle-shaped material 12 may be of an arbitrary value so long as cell clusters are not destroyed and cell cluster fusion is not prevented. Further, in one embodiment, needle-shaped material 12 is a cone-shaped material with the base of the cone contacting the basal surface of substrate 11 (FIG. 1D). Sheet 13 has holes or is a mesh so that it can be penetrated by the thread or needle-shaped material arranged in an almost perpendicular direction on the basal surface of substrate 11, and can be removed from substrate 11 and thread or needle-shaped material 12. The certain embodiment (FIG. 1D) in which needle-shaped material 12 is conical is preferable because it allows easy removal of the sheet from said needle-shaped material. The support of the present invention is, in the main, used for temporary immobilization until cells fuse together in order to obtain a cell structure in the desired shape. In several embodiments, organ simulations and the like are performed while the cell structure is maintained on the support of the present invention. In such instances, the support may be either drawn or not drawn from the cell structure.

Figure 1E:
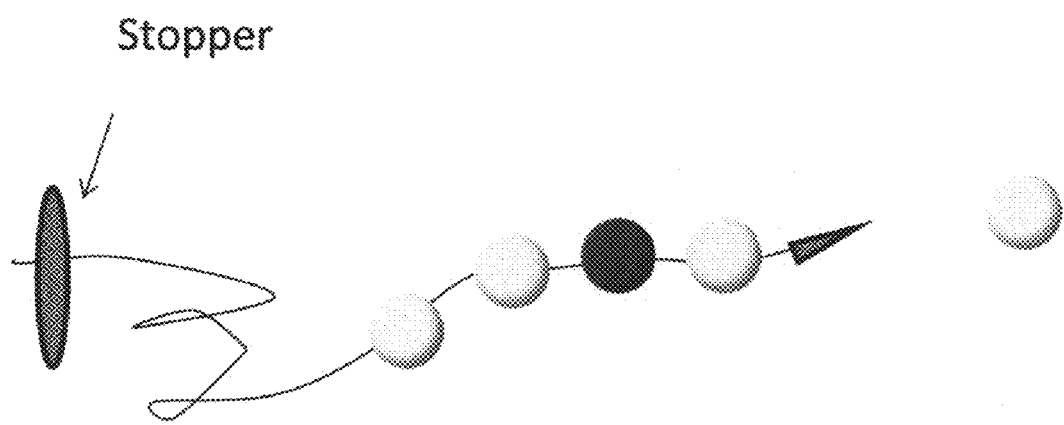
FIG. 1E is a drawing showing an example wherein one end of a thread-shaped material is anchored (for example, using a stopper or the like) and the other end is puncturing cell clusters.
Figure 1F:
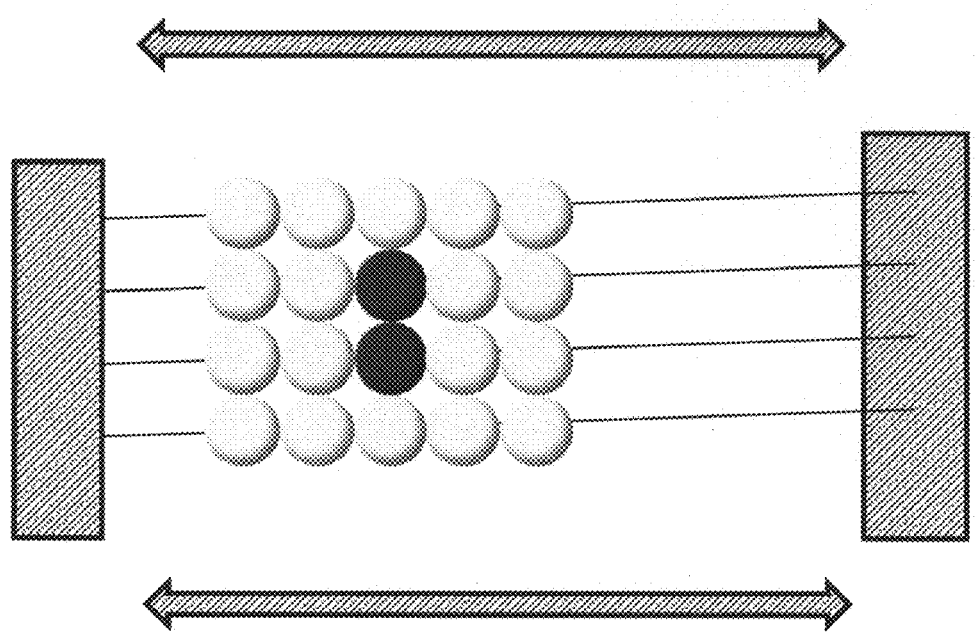
FIG. 1F is a drawing showing an example wherein cell clusters are threaded onto the thread-shaped materials, the thread is anchored in a tense state, and cell clusters are aligned.

Further, in another embodiment, thread-shaped material 12 may be, for example a suture or the like. Preferably, a suture with an attached needle can be used as this thread-shaped material. For example, if one end of a thread is anchored to a substrate, and the other end is a sharp form (such as a needle), it can be made easier for a thread-shaped material to penetrate a cell cluster (FIG. 1E). Further, cell clusters can also be threaded onto the thread, anchored with the thread pulled taut and aligned (FIG. 1F). After a predetermined plurality of cell clusters are penetrated by a thread with one end anchored atop a first substrate in order to form a "shish kebab" state, the end of the thread used to penetrate the cells can be anchored atop a second substrate. Further, the thread that penetrates the cell clusters can be of sufficient length in relation to the distance between the first substrate and the second substrate and anchored so that neighboring cell clusters make contact with each other when the thread is threaded back and forth several times between the first substrate and the second substrate.

2. Cell Clusters

Cells are divided into two main classifications: floating cells and anchorage-dependent cells. The former include hemocyte and immune system cells, while the latter include skin and bone cells. Skin and bone cells will die if floating in culture solution, and must be adhered to a petri dish (such as glass) in order to facilitate propagation. Accordingly, when cells are cultured on the TEFLON®-treated plate, cells seek a scaffolding and adhere to each other, thereby forming cell aggregates, in other words, spheroids. Furthermore, when spheroids adhere to each other and fuse, larger spheroids are formed. For example, when cells are seeded on a non-cell-adherent plate and cultured, the cells will spontaneously aggregate, thereby forming spheroids. Culture time required until spheroids form is 6 to 24 hours, preferably 24 to 48 hours. Cell cluster production methods are not limited to the above. A multitude of methods are known, including the gyratory culture method, wherein a cell suspension is inserted into a gyrating solution; a method wherein a cell suspension is inserted into a test tube and precipitated in a centrifuge; and the alginate bead method. The method wherein a cell suspension liquid is inserted into a water-repellent, non-cell-adherent multiwell when processing and recovering a large quantity of cell clusters is efficient and preferable.

In recent years, reports imply that cell-to-cell adhesion triggers the expression of collagen, etc. during differentiation from mesenchymal stem cells to cartilage cells (Yoon Y M, J Cell Biochem 2002; 87(3): 342-59). Therefore, it is believed that the adhesion of cells to one another as spheroids causes cells to move during the stationary phase of the cell cycle and protein production to increase. Accordingly, in order to induce the stationary phase during which protein production increases in cells, it is preferable to form the predetermined shape after cells have already formed spheroids. The act of differentiating cells after inducing the stationary phase is called "cells separated from growth cycle; move towards cell differentiation".

Cells suitable for spheroids are undifferentiated cells such as stem cells (ES cells, umbilical cord blood-derived cells, undifferentiated mesenchymal stem cells, etc.) or differentiated cells thereof. Since easy differential derivation of osteoblast cells, cartilage cells, and adipose cells from undifferentiated mesenchymal stem cells is possible, these differently derived cells (joint cartilage cells, bone cells, etc.) can also be used. Further, adult mesenchymal cells can also be used. Accordingly, when considering cases in which cell structures produced with the present invention are used for production of tissue fragments which have a three-dimensional shape, examples of three-dimensionally constructed tissues, which are focused on mesodermal system tissues, include joint cartilage and bones, adipose tissue such as breasts, ligaments, tendons, teeth, auricles, and noses. Use is not limited to mesodermal system tissues; almost all adhesive cells such as liver cells, pancreas cells, blood vessel cells, and nerve cells can be used. Further, spheroids need not be formed from an aggregate of a single type of cell, but may be formed from multiple types of cell as long as a spheroid is formed. This type of chimera spheroid can be used to manufacture the cell structures of the present invention.

Mesenchymal stem cells can be harvested from the bone marrow of subject animals (experimental animals such as mice, rabbits, rats, guinea pigs, dogs, pigs, goats, and cows) or humans using a known techniques such as Dexter's method, a magnetic bead method, or a cell-sorting method. Further, mesenchymal stem cells can be harvested from skin, subcutaneous fat, muscle tissue, or the like.

3. Cell Cluster Positioning Method

Figure 2A:
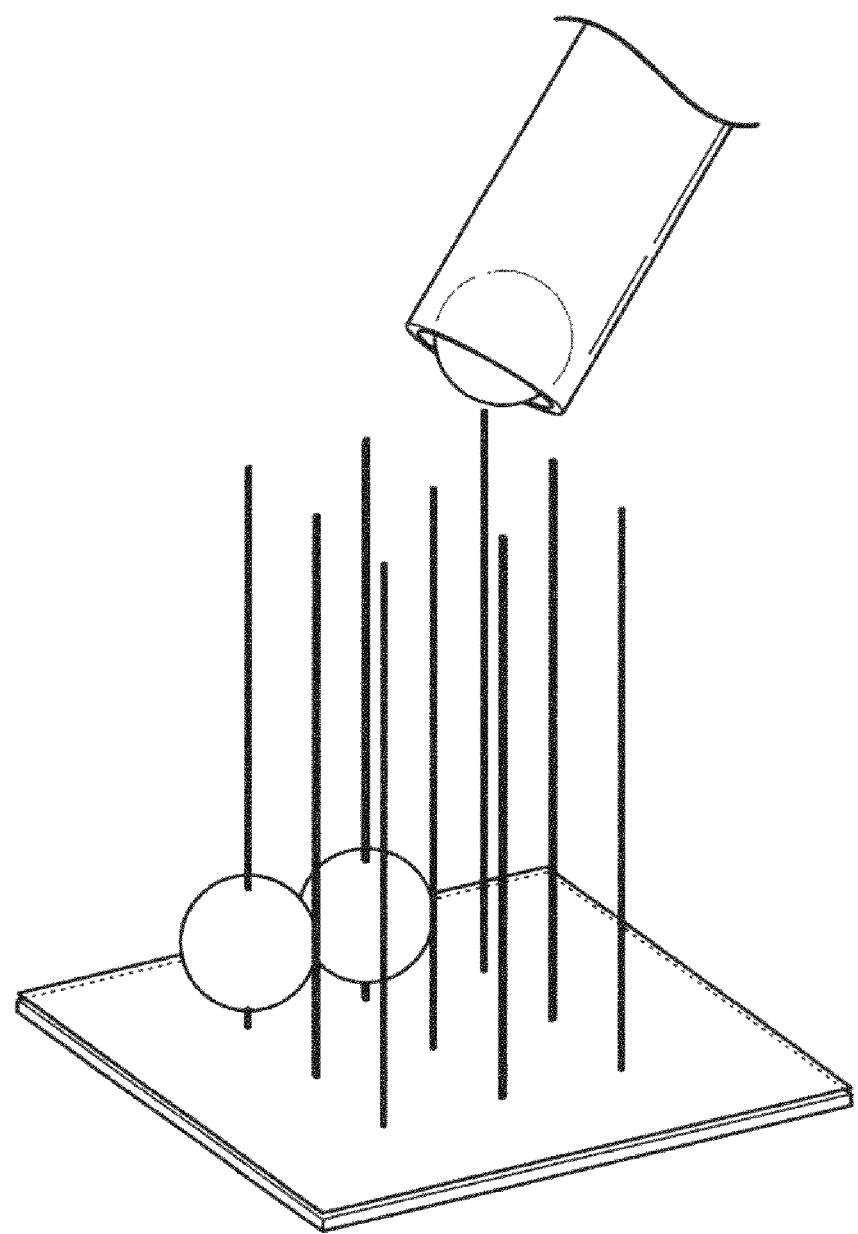
FIG. 2A shows a drawing of cell clusters (spheroids) applied to the support of the present invention using a pipette.
Figure 2B:
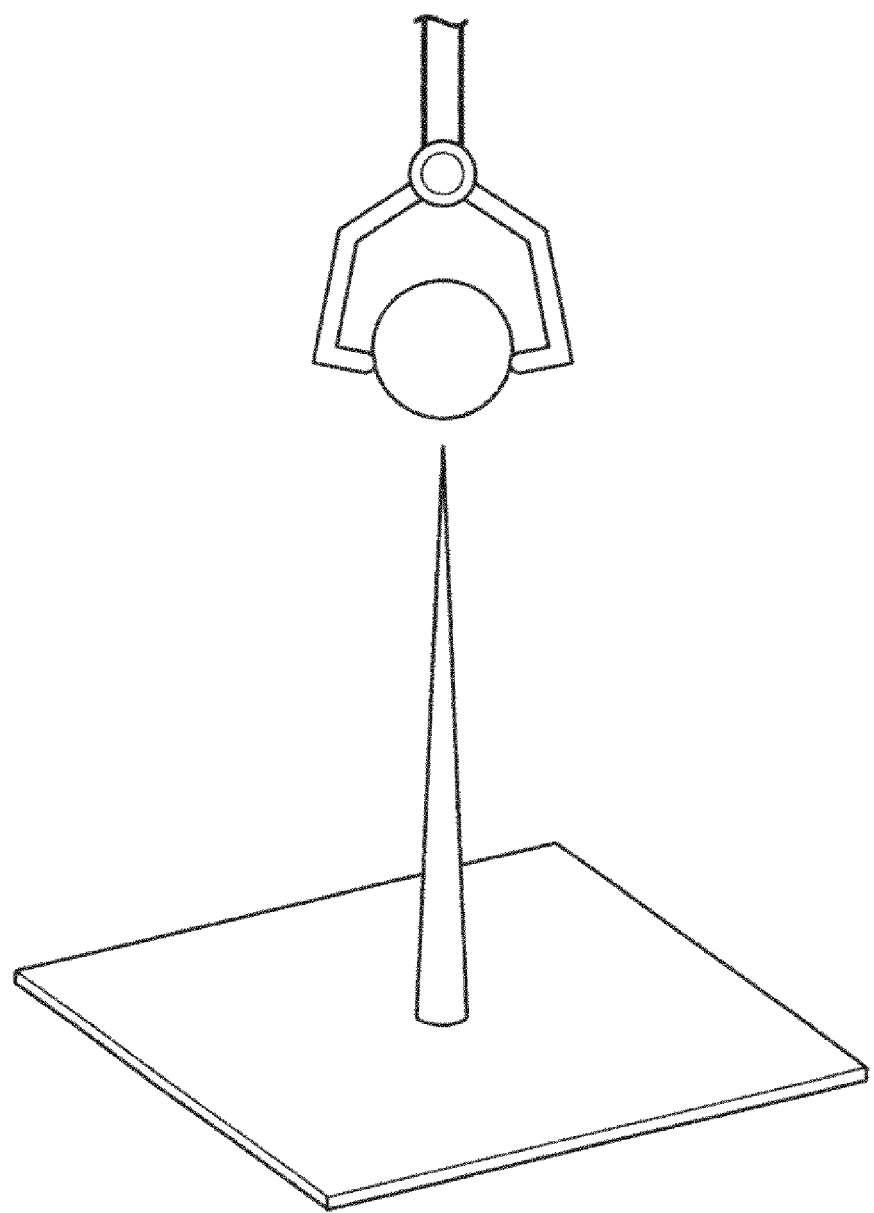
FIG. 2B is a diagram showing a robot arm used to apply cell clusters to a needle-shaped material.
Figure 2C:
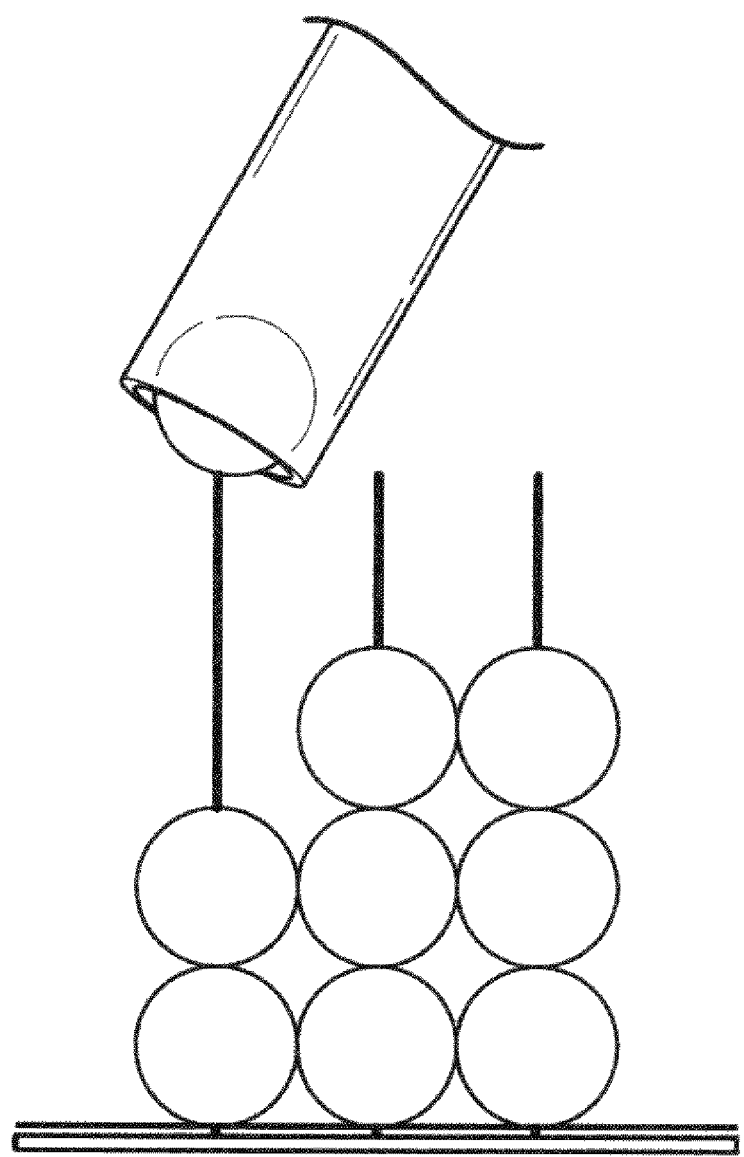
FIG. 2C shows a drawing of penetrated cell clusters atop the support of the present invention as observed from the side.
Figure 2D:
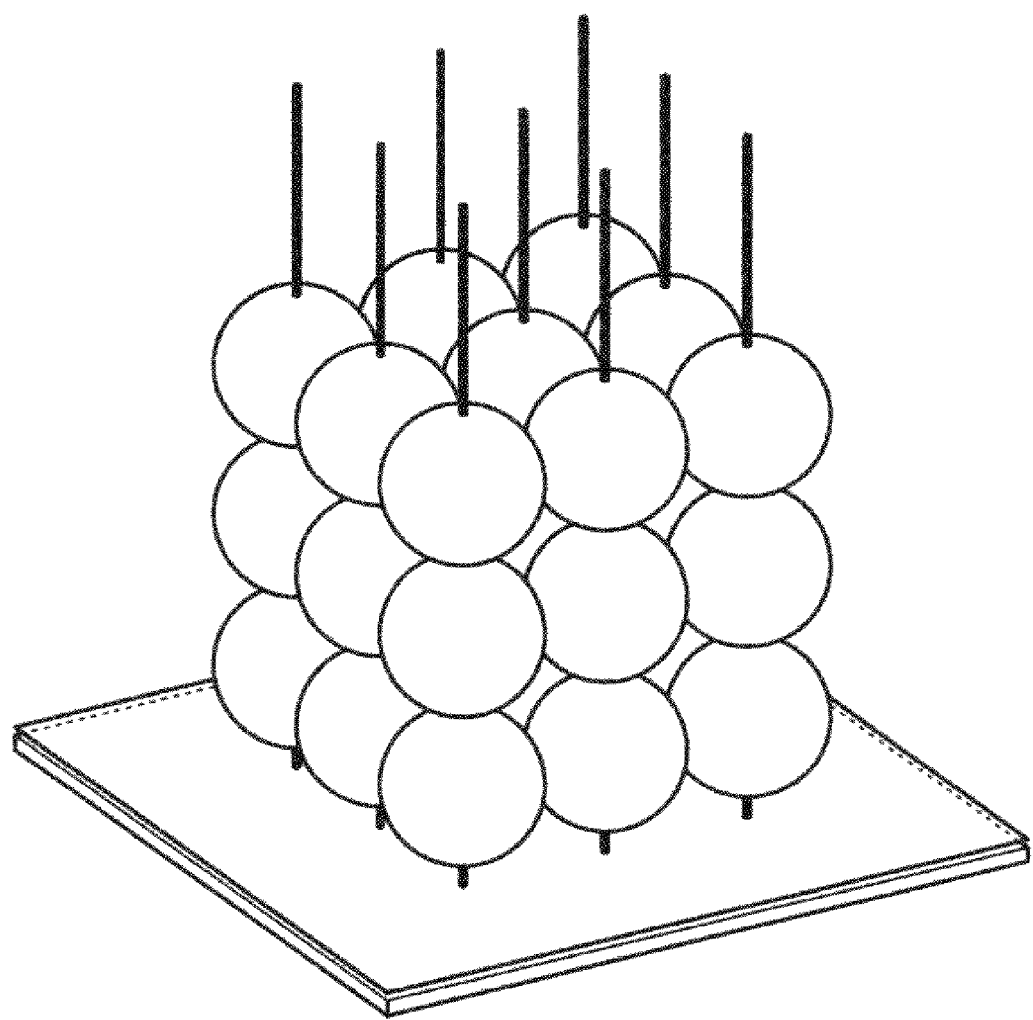
FIG. 2D is a perspective view of penetrated cell clusters atop the support of the present invention.

According to the present invention, cell clusters can be positioned in an arbitrary space above the support through the use of the supports of the present invention. Accordingly, the method of the present invention comprises the steps of
a) forming cell clusters;
b) puncturing the formed cell clusters with the thread or needle-shaped materials of the supports; and
c) causing the penetrated cell clusters to contact each other.
In the first cell cluster forming step, for example, cell clusters are formed by inserting a cell suspension into a gyrating solution. Next, the cell clusters formed through the first step (in other words, the spheroids) are penetrated by a thread or needle-shaped material atop the support. This step can be practiced by, for example, pointing the end of a pipette containing the cell clusters at the end of the needle-shaped materials and applying pressure to the opposite end of the pipette, thereby expelling the cell clusters (FIG. 2A). The expelled cell clusters will be impaled on the needle-shaped materials and anchored in a predetermined position. Alternatively, in another embodiment, this step can be achieved through the use of a small robot arm with the cell clusters thereon that punctures the cell clusters by lowering them onto the needle-shaped materials (FIG. 2B). Further, a thread-shaped material (preferably, a thread with needle) can be used to pierce the cell clusters while the cell clusters are immobilized with tweezers or the like. However, the method of the present invention is not limited to these steps. Cell clusters are penetrated so that multiple cell clusters make contact on a single thread or needle-shaped material (in a so-called shish kabob) (FIG. 2C). Through contact with each other, the cell clusters can fuse in a vertical direction (perpendicular direction (for example, z direction)). Further, since each thread-shaped material or needle-shaped material is positioned at intervals such that the penetrated cell clusters can make contact with the neighboring cell clusters, cell clusters can also make contact and fuse in the horizontal direction (parallel direction and depth direction (for example, x direction and y direction)). Accordingly, through this cell fusion, three-dimensional structures composed of cells are constructed on the support of the present invention (FIG. 2D).

4. Cell Structure Manufacturing Method

Figure 3A:
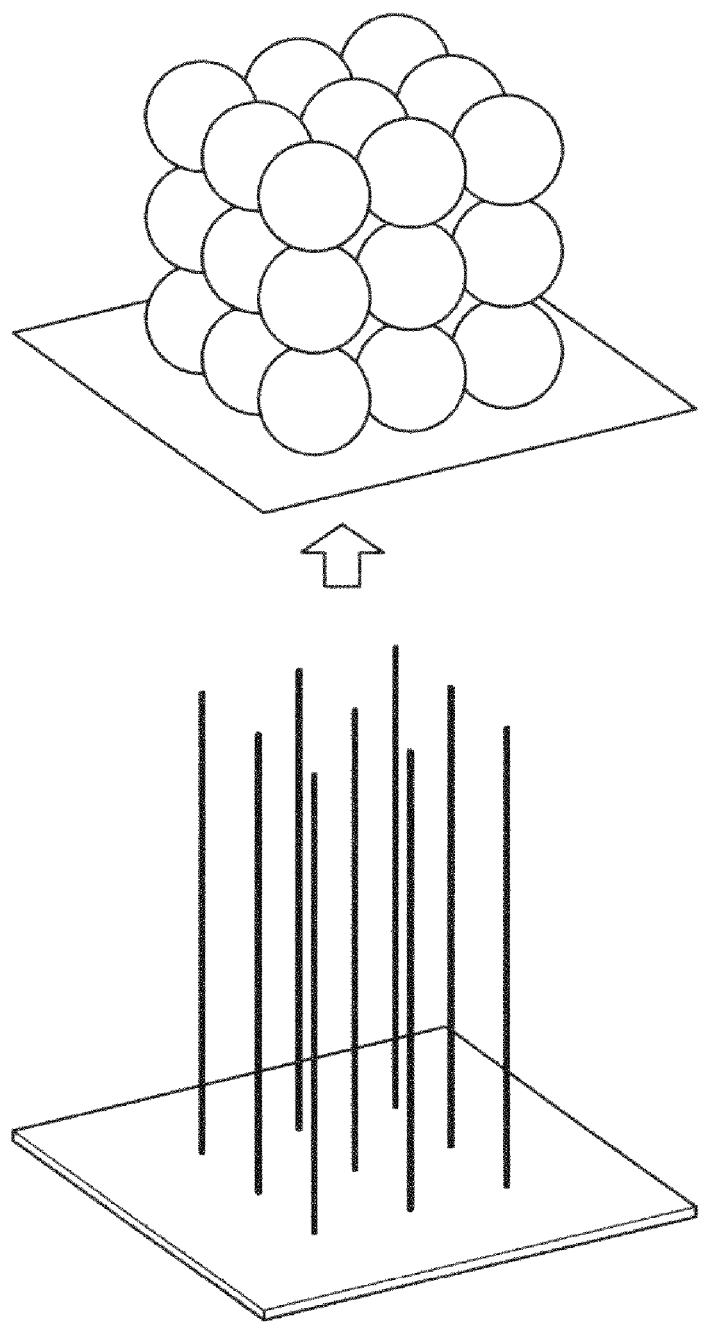
FIG. 3A is an example of the step wherein produced cell clusters are recovered according to the method of the present invention by drawing the fused cell clusters from the supports.
Figure 3B:
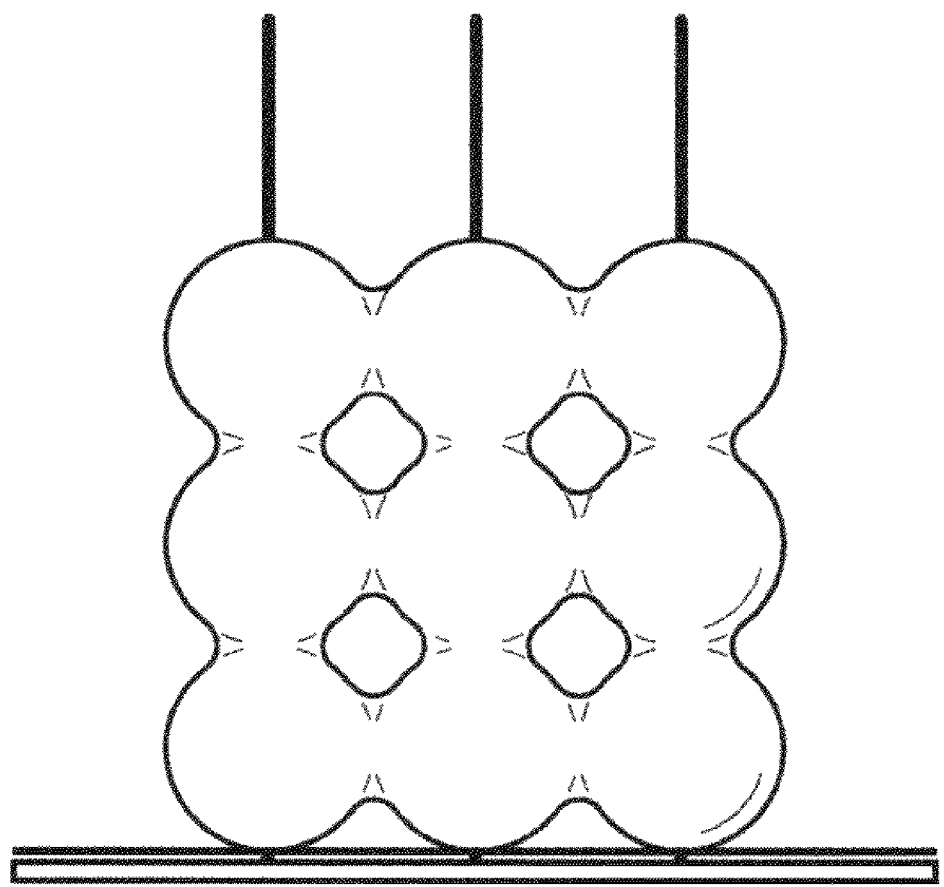
FIG. 3B is a drawing showing an example of a cell cluster produced according to the method of the present invention.

The present invention provides a method for using the supports of the present invention to manufacture cell structures. The manufacture of cell structures is achieved by recovery of the cell clusters that made contact with each other and fused in the steps described above. Recovery of these cell clusters is achieved through the step of drawing the fused cell clusters from the supports (FIG. 3A). Drawing cell clusters from the supports may be achieved by directly immobilizing the cell clusters with tweezers and drawing the thread or needle-shaped material from the fused cell clusters or, alternatively, may be achieved by the step of removing the sheet from the supports. It is sufficient if removal of the sheet is performed by drawing the supports from the immobilized sheet or removal of the sheet from the immobilized supports. A cell structure of arbitrary shape spatially arranged as desired is provided by the method containing the set of these steps (FIG. 3B).

5. Cell Structure

In the present invention, cell structures may be composed of cells of the same type or may contain cells of a plurality of types. As used herein, the term "cells of the same type" means functionally equivalent cells of a single type that are derived from the same tissue, organ, etc. Cell structures containing multiple types of cells can be obtained by applying cell clusters formed from each of the different cell types (i.e. cell cluster A formed from cells a and cell cluster B formed from cells b) to the supports of the present invention. Here, a cells and b cells may be arbitrary cells as long as cells of their clusters are fused together. a cells and b cells may be, for example, homogenous cells derived from different types of tissue (or organs), heterogenous cells derived from the same tissue (or organ), or heterogenous cells derived from different tissues (or organs). In one embodiment, a chimera cell structure comprising cell cluster A and cell cluster B can be provided at the support of the present invention if, where the cell clusters are arranged in a grid pattern, a first row of needle-shaped materials penetrates cell cluster A, a second row of needle-shaped materials penetrates cell cluster B, and the preceding are fused. (FIG. 4A). In a further embodiment, a structure in which cell cluster A and cell cluster B form alternating layers can be produced by alternately applying both cell clusters so that cell cluster A is added to a third row of needle-shaped materials, and cell cluster B is added (hereinafter identical) to a fourth row of needle-shaped materials in addition to the above-described first row and second row (FIG. 4B). Further, it is also possible to change the type of cell cluster that is being penetrated by a single needle-shaped material (FIG. 4C). In an identical method, the three-dimensional composition of chimera cell structures can be controlled by applying cell cluster A and cell cluster B at the desired ratio and in the desired needle-shaped material position. It is sufficient if the different types of cells used are not limited to two, and three or more types of cells are used.

Figure 4D:
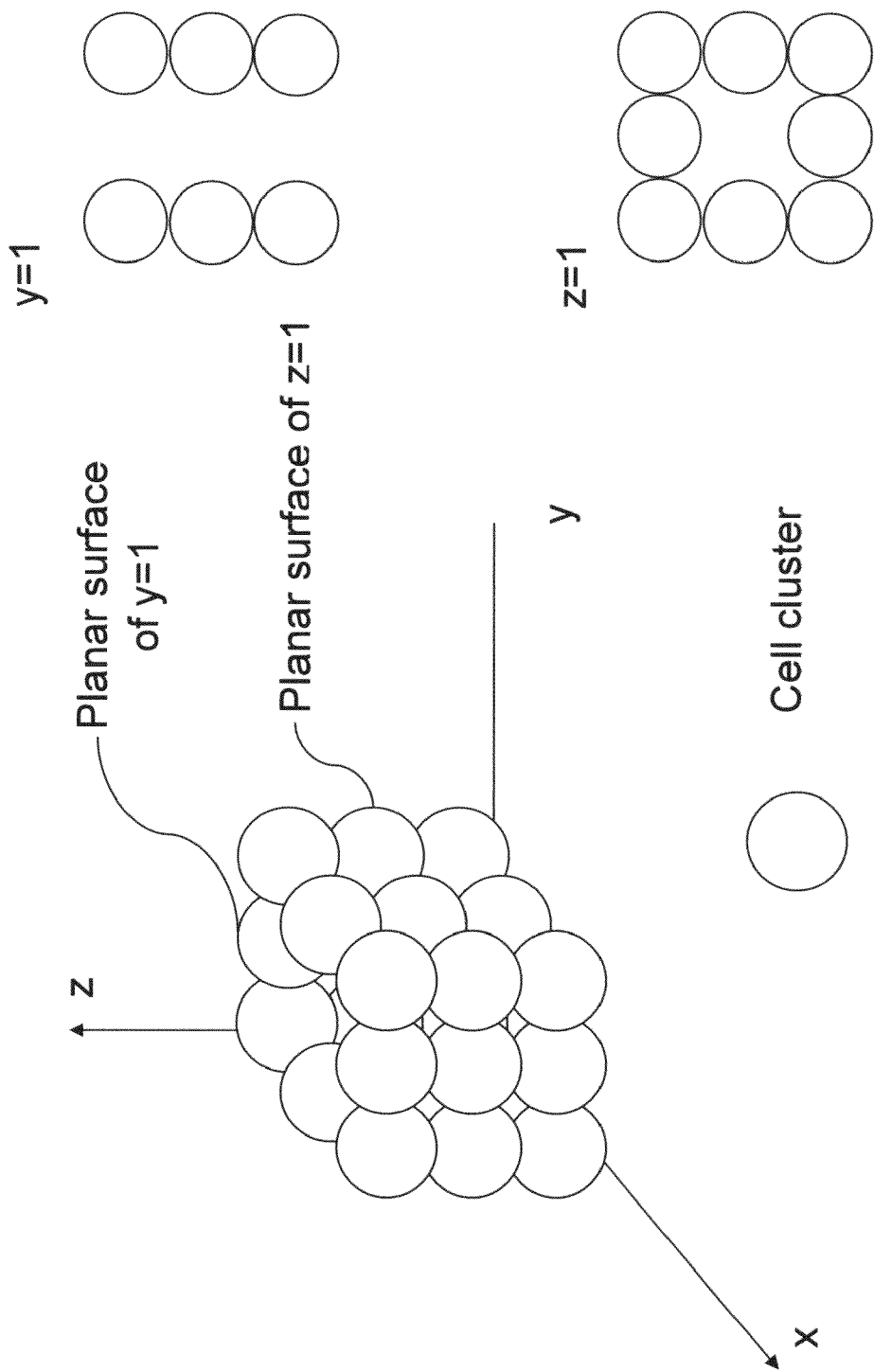
FIG. 4D is a drawing showing a different example of a cell structure having a space within the cell clusters. In this example, cell structures having a void space at their interior in which no cells exist can be manufactured. This cell structure does not cause all cells to make continuous contact when cells are applied to the support of the present invention. A void space can be provided by removing the region atop the needle-shaped material where a void space is desired, arranging cell clusters in the vicinity thereof, and causing fusion.

In yet another example, cell structures having a void space at their interior in which no cells exist can be manufactured by the method of the present invention. This cell structure does not cause all cells to make continuous contact when cells are applied to the support of the present invention. A void space can be provided by removing the region atop the needle-shaped material where a void space is desired, arranging cell clusters in the vicinity thereof, and causing fusion. Although this void space at the interior of cell structures can be arbitrarily designed, preferably the wall surfaces of the structure are composed of cell clusters and the interior thereof can be hollowed into a tubular (tunnel) form (FIG. 4D). Since configuring this sort of void space at the interior of cell structures allows the nutrients, oxygen, etc. contained in the culture solution to pass through the space and thereby reach the cells at the interior of the cell cluster, cell structures that have a void space have an advantage when it is necessary to produce cell structures with a larger volume.

6. Cell Structures for Use in Medical Treatment or Experiments

Cell structures of the present invention can be used in regenerative medicine or in experiments. If cell clusters of cartilage cells are used to form a cell structure, said structure can be used in joint regenerative medicine by being transplanted into a joint lost as a result of joint wear, an accident, etc.

In addition to the above-mentioned examples, research on spheroids containing liver cells is being vigorously pursued at the present time. Accordingly, using cell clusters of liver cells to form cell structures makes it possible for the cell structures that are formed in regenerative medicine to be used in the liver. However, the structures of the present invention are not limited to the above-mentioned organs and can be targeted at all organs for which regenerative medicine is desired.

Furthermore, spheroids having a three-dimensional structure are known for better reflecting the in vivo behavior of many types of cells in comparison with conventional two-dimensional cultures, and use of spheroids in research on the interaction between tumor and immune system cells and screening for drug development, etc. is reported. Accordingly, cell structures manufactured according to the present invention can be used in applications for artificial organs, various cell assays, screening, and other types of experiments.

EXAMPLES

1. Spheroid Production

Bone marrow-derived mesenchymal stem cells obtained from the pelvis of a rabbit were cultured as a monolayer. Ultimately, $1.0 \times 10^6$ mesenchymal cells were obtained per 15 cm dish. These cells were treated with trypsin, made into a cell suspension, and seeded so that $1.0\times10^5$ cells would fit into each spheroid plate made by Sumitomo Bakelite Co., Ltd. Thereafter, culturing was performed under 37° C. and 5% $CO_2$ conditions, and cell clusters with an average diameter of 0.3 mm were prepared the following day.

2. Cell Structure Production (1)

Figure 5:
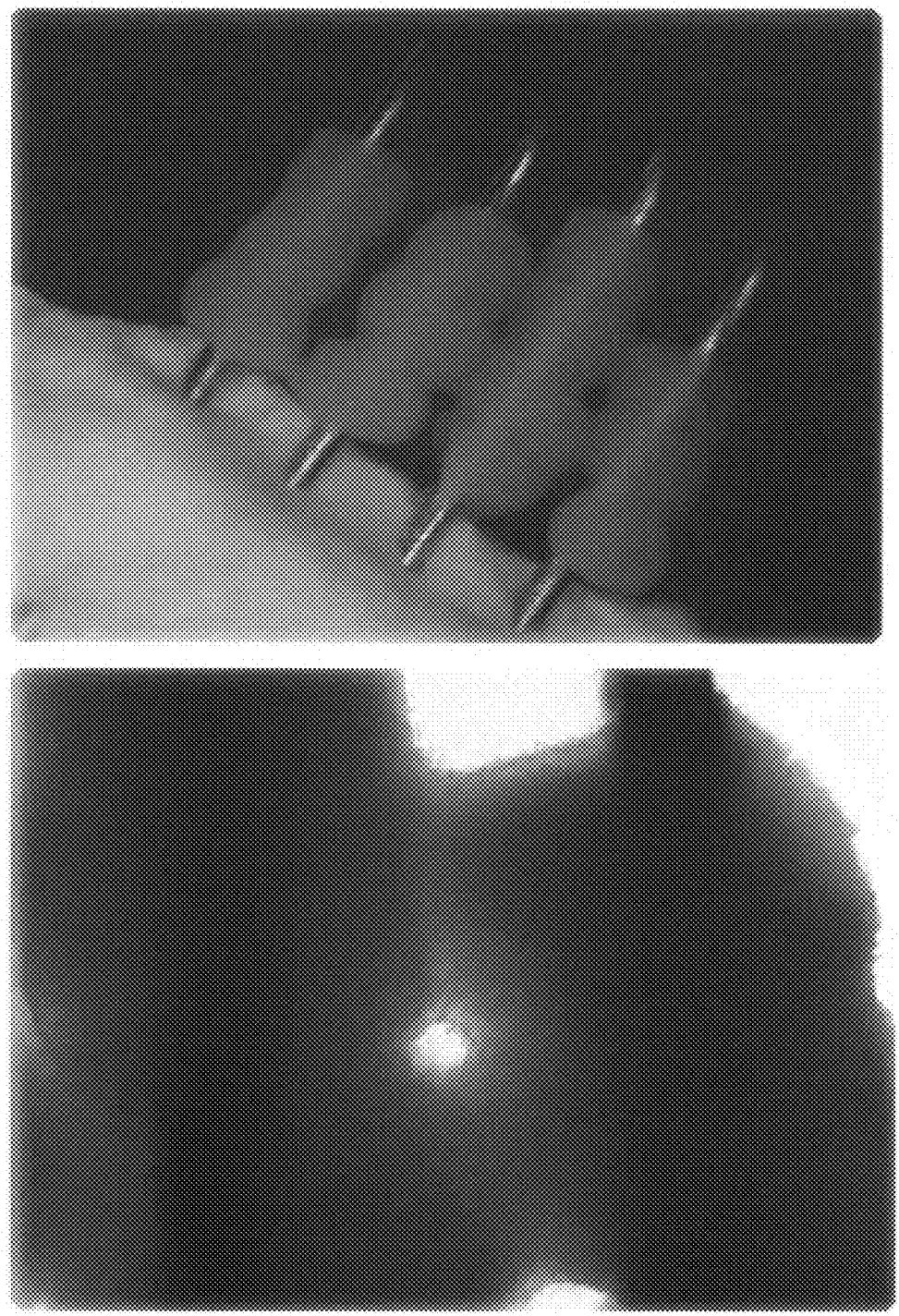
FIG. 5 shows microscopic images of fused cell clusters.

The stainless steel portion of four Terumo Corporation 33 G injection needles (product name: Nanopath) were horizontally immobilized to Mitsubishi Pharma Corporation α-tricalcium phosphate (product name: Biopex R) thereby producing a support. While viewing under a stereomicroscope, sharp tweezers were used to insert the spheroids one at a time onto the tip of the stainless steel needles immobilized to the support. Following insertion, spheroids were cultured under 37° C. and 5% $CO_2$ conditions. Approximately two days later, cell structures wherein neighboring spheroids had fused (bonded) in the vertical direction and horizontal direction were observed (FIG. 5).

3. Cell Structure Production (2)

Figure 6:
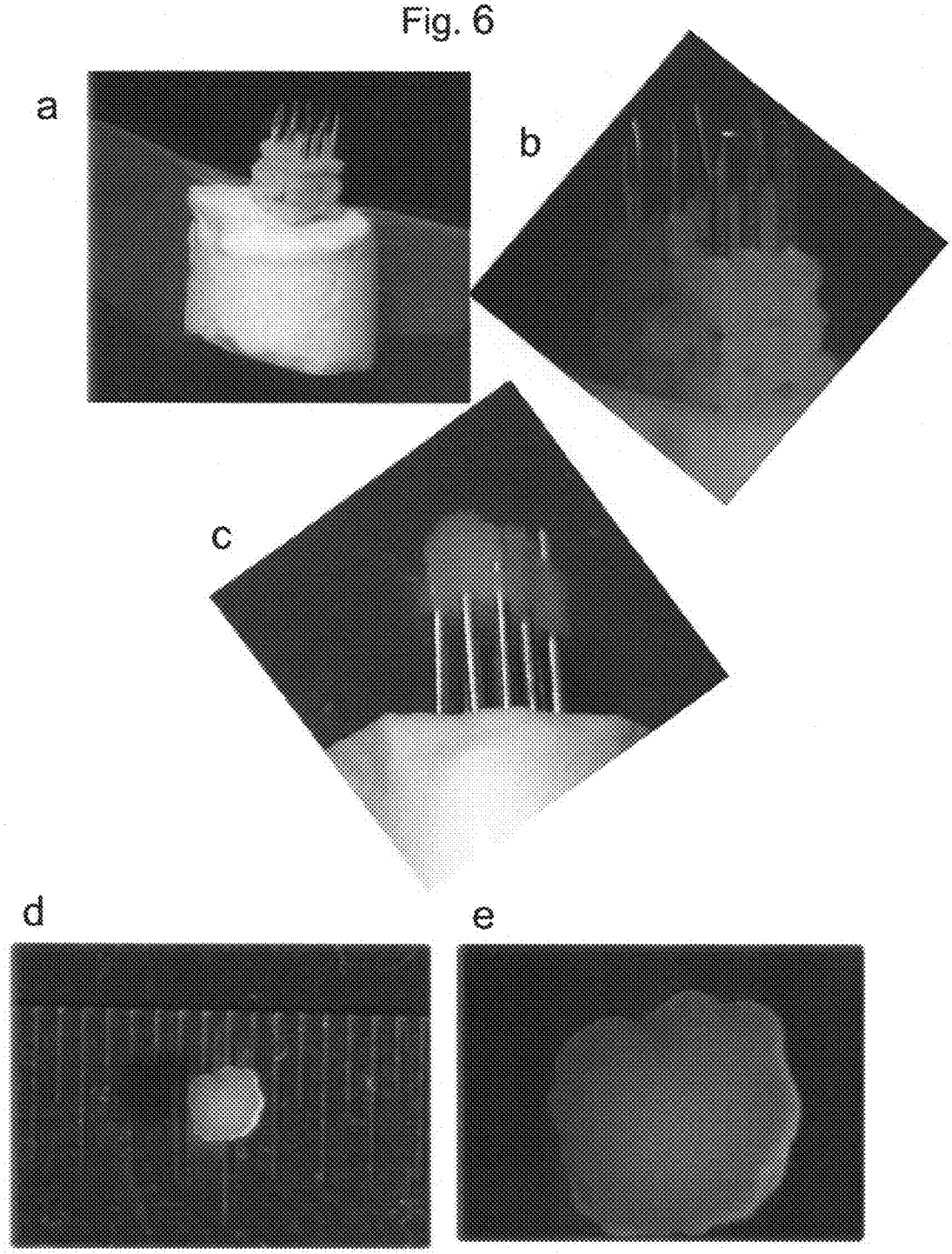
FIG. 6 shows images of the chronological flow until cell clusters are obtained in one embodiment in order to obtain a cell structure of the present invention.

The stainless steel portion of a total of nine Terumo Corporation 33 G injection needles (product name: Nanopath) were immobilized in the perpendicular direction to Mitsubishi Pharma Corporation a-tricalcium phosphate (product name: Biopex R) 0.4 mm apart in a 3×3 grid to produce a support. At the upper surface of the support, a BD Falcon filter (product name: cell culture insert; polyethylene terephthalate) size 8.0 μm, product number 353093) is punctured with a needle and positioned at the basal portion of the needle. While viewing under a stereomicroscope, sharp tweezers are used to insert spheroids produced as in the description in the paragraph "1. Spheroid production" above (approximately 50) one by one onto the needle of the support (FIG. 6, a). Following insertion, culturing was performed under 37° C., 5% $CO_2$ conditions, and cell structures comprising neighboring spheroids fused (bonded) to each other in both the vertical and horizontal directions were confirmed approximately three days later (FIG. 6, b). After cell structure confirmation, sharp tweezers were used to slowly draw from the support both the filter that was placed beforehand between said support and the cell structure and the fused cell structure, thereby recovering the cell structure (FIG. 6, c). The obtained cell structure is a single, large fused cluster (diameter, approximately 3 mm) (FIG. 6, d and e).

4. Cell Structure Production (3)

Qtracker (product name) 655 (red) and 565 (green) which are part of the viable cell labeling kit series made by Invitrogen Corporation were separately introduced into the parenchyma cells, thereby preparing spheroids that emit red or green, respectively, when observed under a fluorescent microscope.

While viewing under a stereomicroscope, sharp tweezers were used to insert the spheroids one at a time, alternating red and green, onto the tip of the aforementioned four needles immobilized to the support. Following insertion, culturing was performed under 37° C., 5% $CO_2$ conditions, and cell structures comprising neighboring spheroids fused (bonded) to each other in both the vertical and horizontal directions were confirmed approximately two days later (FIG. 7A, a).

Figure 7A:
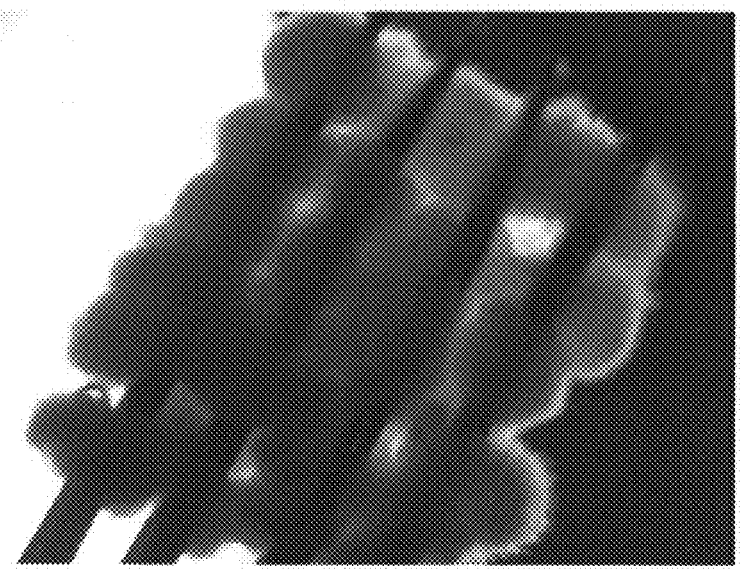
FIGS. 7A to 7E are microscopic images of fused cells in accordance with the present invention.
Figure 7A:
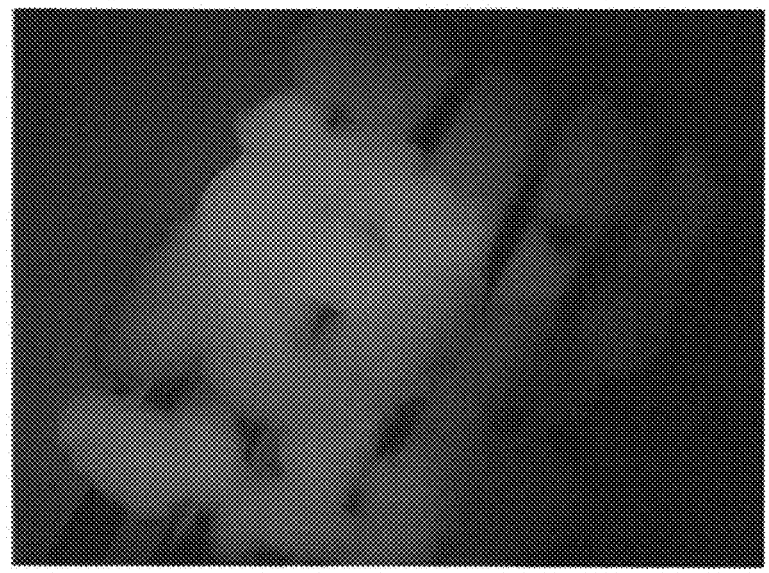

Further examination under a fluorescence microscope revealed cell structures with the intended coloration (FIG. 7A, b).

The stainless steel portion of a total of 25 Terumo Corporation 33 G injection needles (product name: Nanopath) were immobilized in the perpendicular direction to Mitsubishi Pharma Corporation α-tricalcium phosphate (product name: Biopex R) 0.4 mm apart in a 5×5 grid to produce a support structure. At the upper surface of the support, a BD Falcon filter (product name: cell culture insert; polyethylene terephthalate) size 8.0 μm, product number 353093) is punctured with a needle and positioned at the basal portion of the needle. Cell structures in the various forms described hereinbelow were produced using this support (FIG. 7B to FIG. 7D).

Figure 7B:
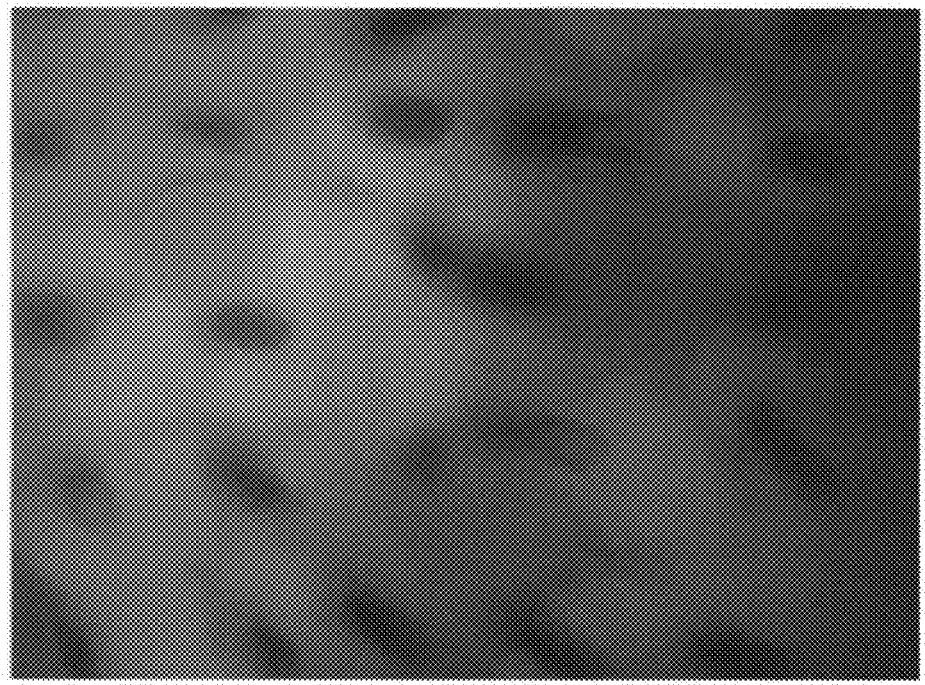
Figure 7C:
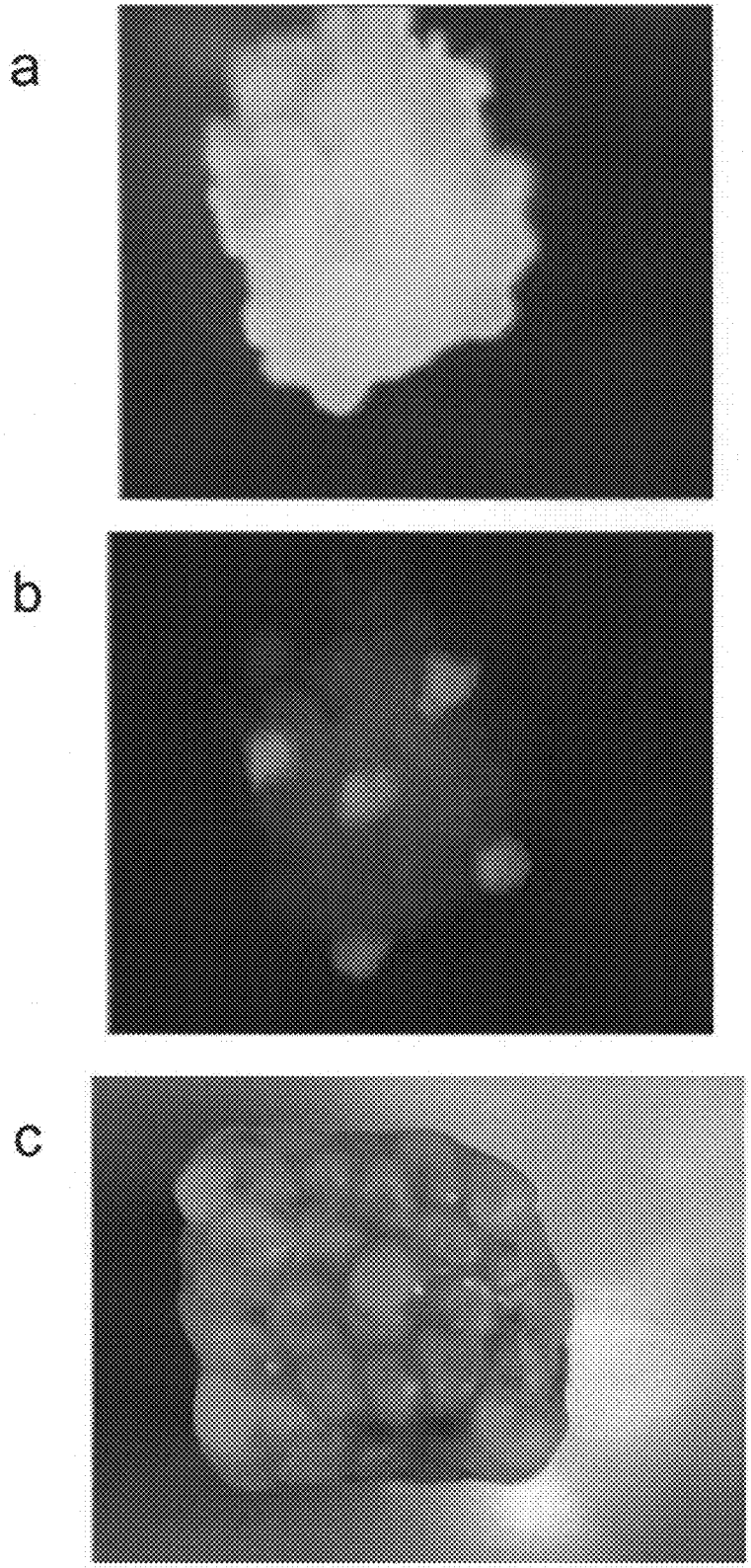
Figure 7D:
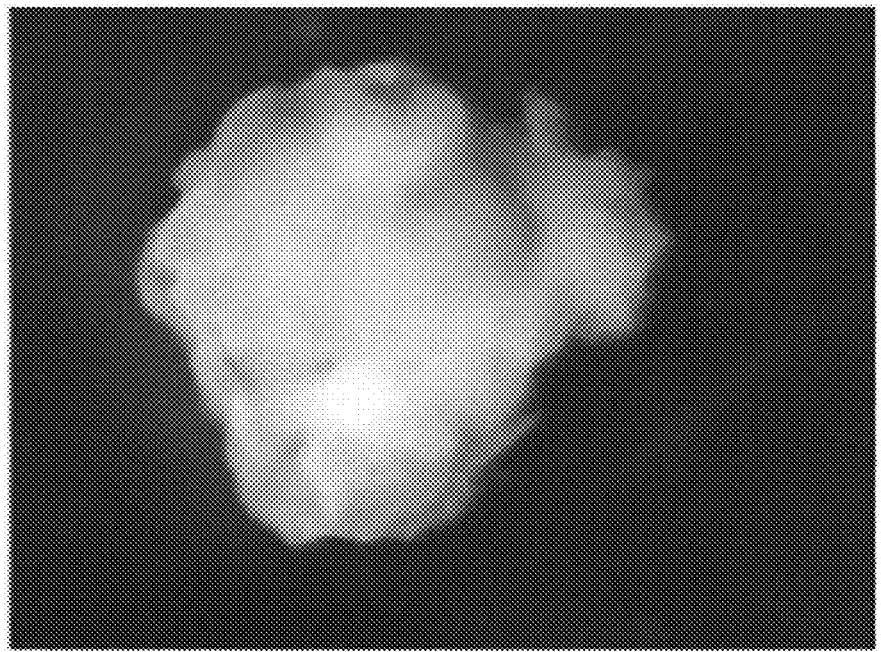
Figure 7D:
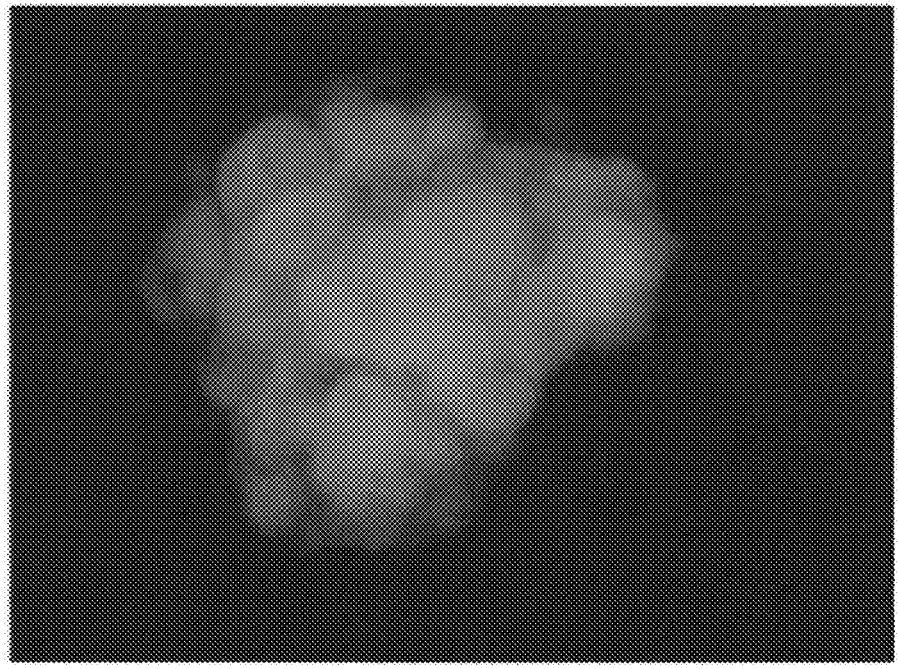

FIG. 7B Cross Pattern

A cube-shaped cell structure was produced, and spheroids that emit the color red were arranged in a cross shape thereon.

FIG. 7C:

A cube-shaped cell cluster was prepared having vascular cells arranged at its apex and center so that it resembles a liver tissue (lobulus hepatis) and having spheroids that emit the color red arranged at the apex of its four corners and on the center of its faces.

FIG. 7D:

A cube-shaped cell structure was produced, and spheroids that emit the color red were arranged in a cross shape thereon.

Figure 7E:
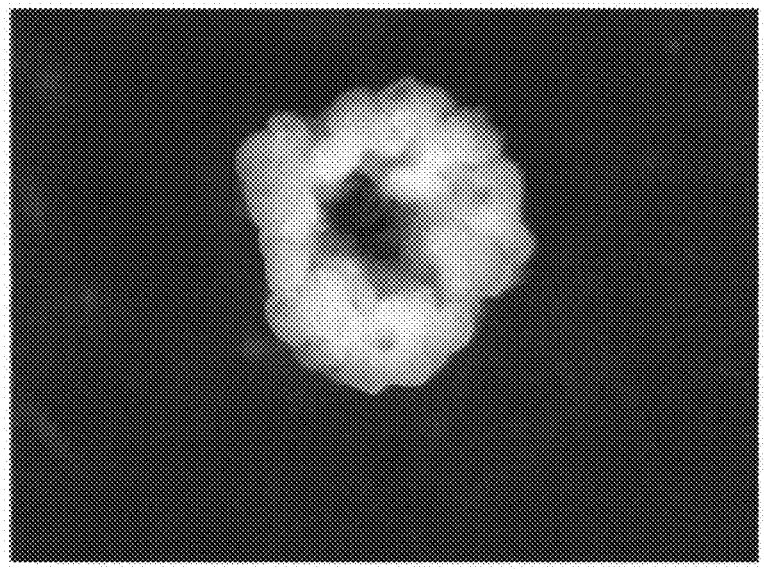
Figure 7E:
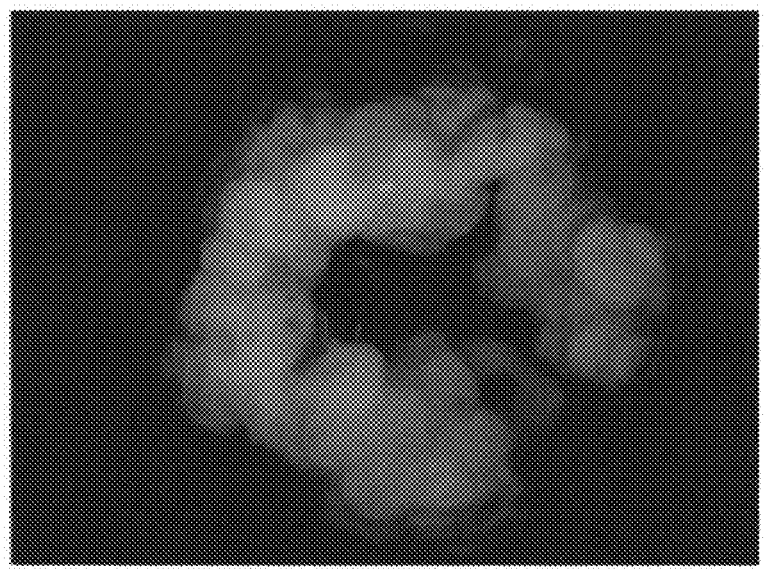

The stainless steel portion of Terumo Corporation 33 G injection needles (product name: Nanopath) were positioned above the circular arc of a dual concentric circle with a 0.3 mm and a 0.7 mm diameters and immobilized to Mitsubishi Pharma Corporation α-tricalcium phosphate (product name: Biopex R), thereby producing a support. Bicolored, cylindrical cell structures with a cavity inside were produced. This imitates a blood vessel, in which the interior is vascular endothelium and the exterior is smooth muscle (FIG. 7E).

Figure 8:
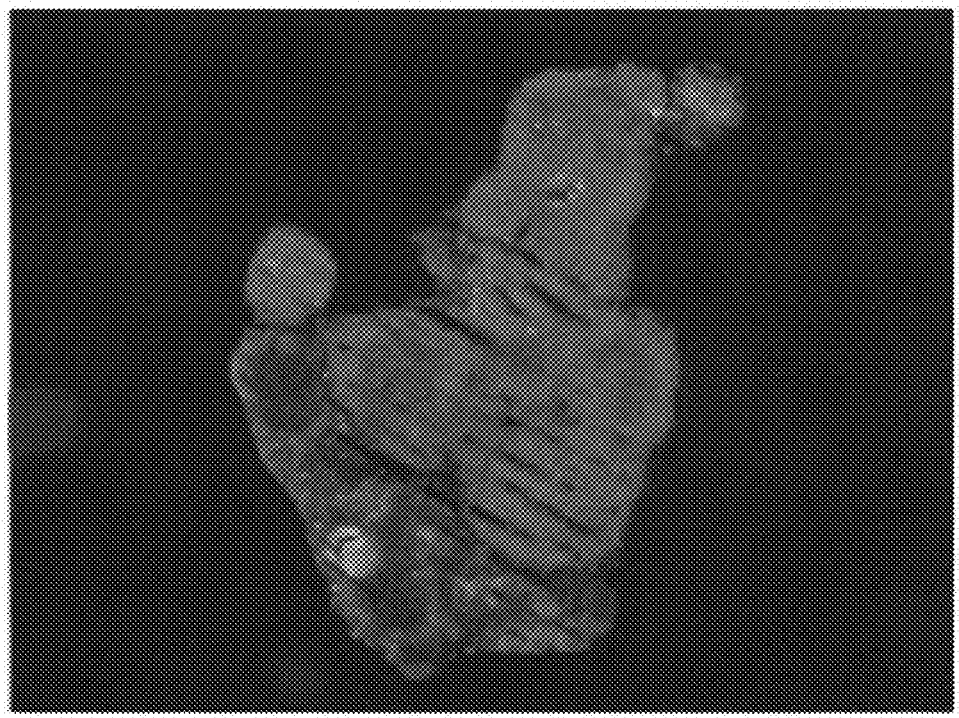
FIG. 8 is a cross-section for observing the interior of a cell structure in which there was no cavity and almost all cells were alive.

The above-described two-color spheroid cell structure having a cross pattern thereon was inserted into liquid nitrogen and frozen instantly. The frozen structure was sliced, and the cross-sections were observed under a fluorescence microscope. Since there are no blood vessels inside the cell structures, it was feared that the cells on the interior would die of malnutrition, thereby causing the interior of the structure to degrade and a cavity to form. However, observation of a section revealed no cavity and confirmed that almost all cells were alive (FIG. 8).

5. Cell Structure Production (4)

Figure 9A:
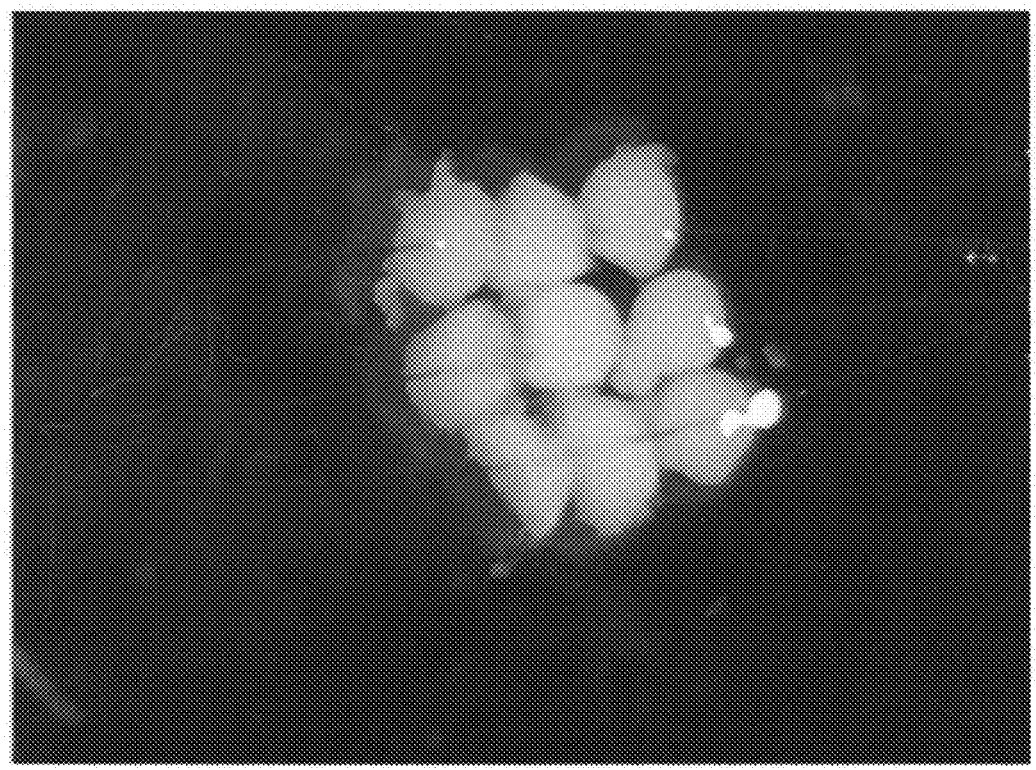
FIG. 9A a drawing of cell clusters penetrated by sutures with attached needles.

A rectangular portion of the mesh on the bottom face of BD Falcon™ cell strainer (model number 352360) was cut and removed. The cell strainer was inverted, the end of a suture (Alfresa Pharma Corporation Nesco Suture™ size: 9-0 nylon) with an attached needle was tied to the end of the cut mesh under a stereomicroscope and anchored in place. While using a stereomicroscope to observe the spheroids produced as described in the paragraph "1. Spheroid production" above, sharp tweezers were used and three spheroids were penetrated with the end (in other words, the tip) of a needle attached to a suture thread (9-0 nylon) and arrange the spheroids so they could fuse together. The thread was tied opposite the cut end of the mesh to which the thread was first tied, penetrated through three spheroids in the same way, and a total of three threads were passed through (FIG. 9A).

Figure 9B:
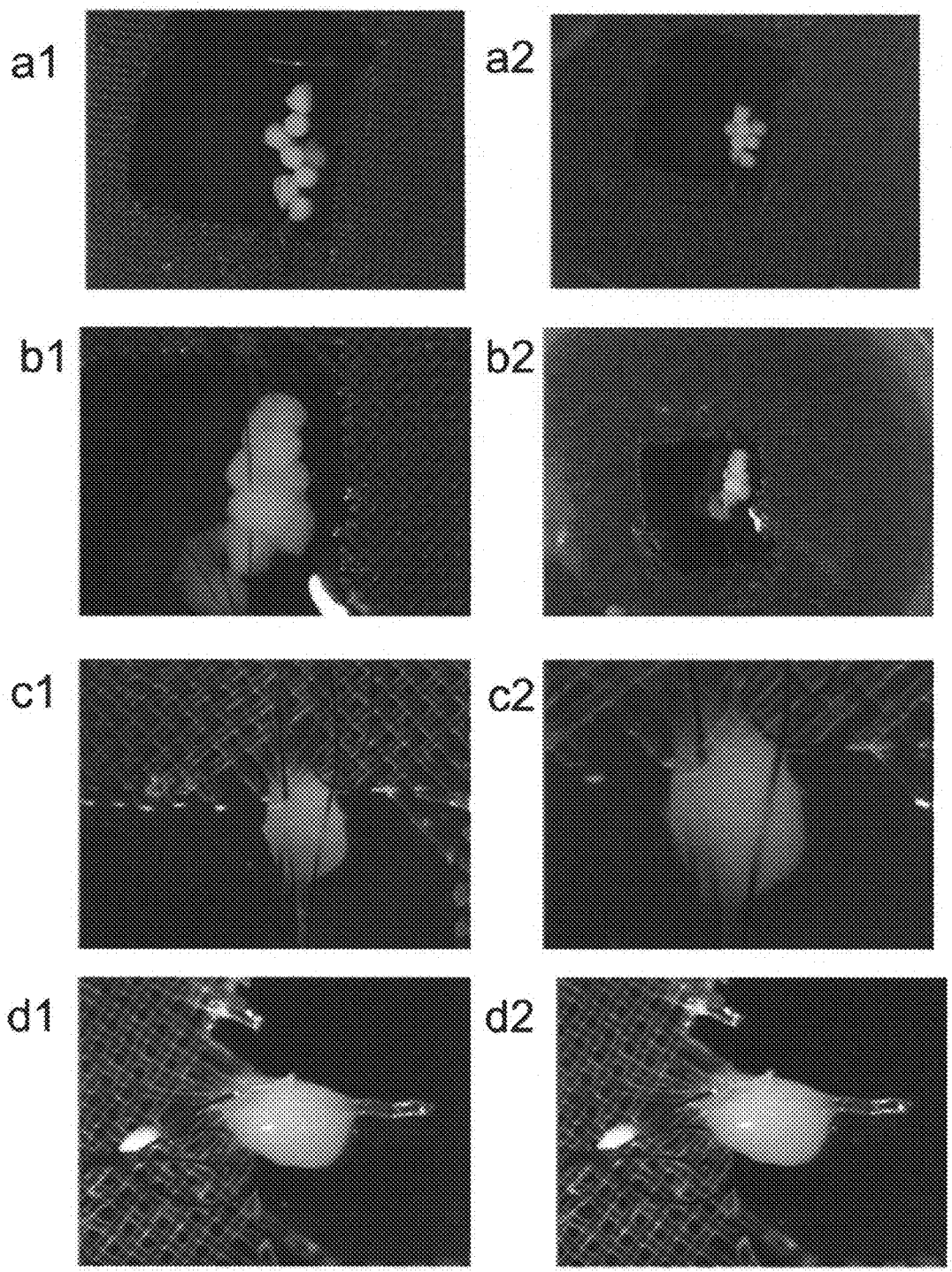
FIG. 9B is a diagram showing the chronological flow until a cell structure is obtained using a suture with an attached needle. The thread was adjusted and arranged so that the spheroids punctured by the thread could fuse in not only the vertical direction but also the horizontal direction (FIG. 9B, $a1$ and $a2$). Following insertion, culturing was performed and it was observed the following day that neighboring spheroids had begun to fuse together ($b1$ and $b2$). Approximately three days later, cell structures comprising neighboring spheroids fused (bonded) to each other in both the vertical and horizontal directions were confirmed ($c1$ and $c2$). After confirmation of the cell structure, the thread was cut, the thread remaining inside the cell structure was pulled out while the cell structure was held down with tweezers, and the cell structure was recovered ($d1$ and $d2$).

The thread was adjusted and arranged so that the spheroids punctured by the thread could fuse in not only the vertical direction but also the horizontal direction (FIG. 9B, a1 and a2). Following insertion, culturing was performed under 37°

Figure 9C:
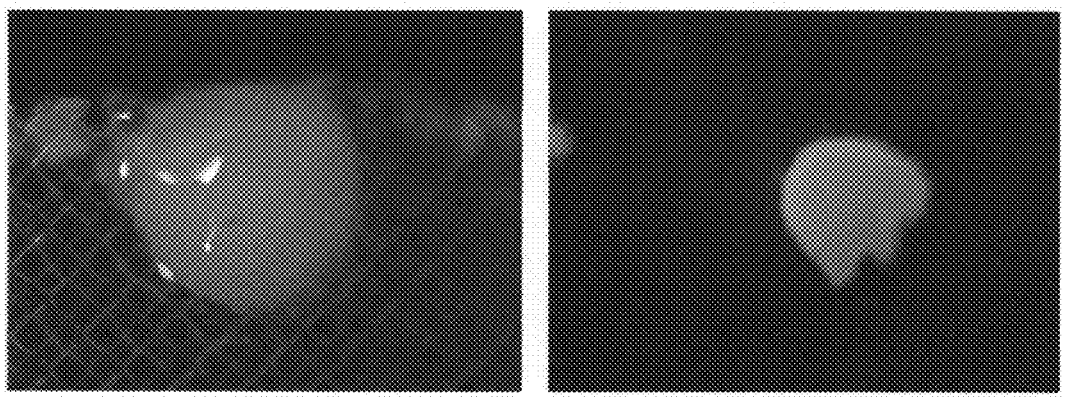
FIG. 9C is an example of a cell structure of the present invention showing a single large fused cluster.

C., 5% $CO_2$ conditions, and it was observed the following day that neighboring spheroids had begun to fuse together (*b*1 and *b*2). Approximately three days later, cell structures comprising neighboring spheroids fused (bonded) to each other in both the vertical and horizontal directions were confirmed (*c*1 and *c*2). After confirmation of the cell structure, the thread was cut, the thread remaining inside the cell structure was pulled out while the cell structure was held down with tweezers, and the cell structure was recovered (*d*1 and *d*2). The obtained cell structure was a single large fused cluster (FIG. 9C).

The invention claimed is:

1. A method for the production of a structure made of cells, comprising:
   a) forming a plurality of cell clusters;
   b) arranging the cell clusters on a support comprising a substrate and a plurality of puncturing structures suitable for puncturing cell clusters selected from thread-shaped and needle-shaped materials, wherein the cell clusters are arranged on the support by penetrating individual cell clusters with a puncturing structure of the support;
   c) causing each penetrated cell cluster to contact at least one other cell cluster, wherein the contact between any two cell clusters occurs either between cell clusters on the same puncturing structure, or between cell clusters on adjacent puncturing structures;
   d) allowing the contacted cell clusters to adhere to each other to form a structure made of cells; and
   e) removing the structure made of cells from the support.

2. The method of claim 1, wherein the puncturing structures are arranged perpendicular to the substrate.

3. The method of claim 1, wherein the puncturing structures are curved.

4. The method of claim 1, wherein the one or more cell clusters is spheroid.

5. The method of claim 1, wherein a single type of cell cluster is used.

6. The method of claim 1, wherein multiple types of cell clusters are used.

7. The method of claim 1, wherein the cell clusters are derived from stem cells.

8. The method of claim 1, wherein removing the structure made of cells occurs by drawing the support from the structure made of cells.

9. The method of claim 1, where in the support further comprises a sheet disposed at the base of the puncturing structures suitable for preventing contact between the substrate and the cell clusters.

10. A method for the production of a structure made of cells, comprising:
    a) forming a plurality of cell clusters;
    b) arranging the cell clusters on a support comprising a substrate and a plurality of puncturing structures suitable for puncturing cell clusters selected from thread-shaped and needle-shaped materials, wherein the arranging occurs by impaling individual cell clusters with a puncturing structure of the support;
    c) causing each impaled cell cluster to contact at least one other cell cluster, wherein the contact between any two cell clusters occurs either between cell clusters on the same puncturing structure, or between cell clusters on adjacent puncturing structures;
    d) allowing the contacted cell clusters to adhere to each other to form a structure made of cells; and
    e) removing the structure made of cells from the support.

11. The method of claim 10, wherein the puncturing structures are arranged perpendicular to the substrate.

12. The method of claim 10, wherein the puncturing structures are curved.

13. The method of claim 10, wherein the one or more cell clusters is spheroid.

14. The method of claim 10, wherein a single type of cell cluster is used.

15. The method of claim 10, wherein multiple types of cell clusters are used.

16. The method of claim 10, wherein the cell clusters are derived from stem cells.

17. The method of claim 10, wherein removing the structure made of cells occurs by drawing the support from the structure made of cells.

18. The method of claim 10, where in the support further comprises a sheet disposed at the base of the puncturing structures suitable for preventing contact between the substrate and the cell clusters.

* * * * *